United States Patent
Ghosh et al.

(10) Patent No.: US 11,944,461 B2
(45) Date of Patent: Apr. 2, 2024

(54) GENERATING REPRESENTATIVE CARDIAC INFORMATION

(71) Applicant: Medtronic, Inc., Minneapolis, MN (US)

(72) Inventors: Subham Ghosh, Blaine, MN (US); Karen J. Kleckner, Blaine, MN (US); Marc C. Steckler, Lino Lakes, MN (US); Trent M. Fischer, St. Paul, MN (US); Daniel S. Flo, Shorewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 245 days.

(21) Appl. No.: 17/107,551

(22) Filed: Nov. 30, 2020

(65) Prior Publication Data

US 2021/0161475 A1 Jun. 3, 2021

Related U.S. Application Data

(60) Provisional application No. 62/942,555, filed on Dec. 2, 2019.

(51) Int. Cl.
| | |
|---|---|
| *A61B 5/35* | (2021.01) |
| *A61B 5/00* | (2006.01) |
| *A61B 5/364* | (2021.01) |
| *A61B 5/367* | (2021.01) |
| *G16H 40/67* | (2018.01) |
| *G16H 50/30* | (2018.01) |
| *A61B 5/256* | (2021.01) |
| *A61B 5/257* | (2021.01) |

(Continued)

(52) U.S. Cl.
CPC .............. *A61B 5/7221* (2013.01); *A61B 5/35* (2021.01); *A61B 5/364* (2021.01); *A61B 5/367* (2021.01); *A61B 5/7203* (2013.01); *G16H 40/67* (2018.01); *G16H 50/30* (2018.01); *A61B 5/256* (2021.01); *A61B 5/257* (2021.01); *A61B 5/341* (2021.01); *A61N 1/36507* (2013.01)

(58) Field of Classification Search
CPC .............................. A61B 5/7221; A61B 5/35
USPC .................................................. 600/508–509
See application file for complete search history.

(56) References Cited

U.S. PATENT DOCUMENTS

| | | | |
|---|---|---|---|
| 4,428,378 | A | 1/1984 | Anderson et al. |
| 5,052,388 | A | 10/1991 | Sivula et al. |
| 6,980,675 | B2 | 12/2005 | Evron et al. |

(Continued)

OTHER PUBLICATIONS

International Search Report and Written Opinion from PCT Application No. PCT/US2020/062616 dated Feb. 25, 2021, 9 pages.

(Continued)

*Primary Examiner* — Nicole F Lavert
*Assistant Examiner* — Nicole F Johnson
(74) *Attorney, Agent, or Firm* — Mueting Raasch Group

(57) ABSTRACT

Systems and methods are described herein for generating representative cardiac information. The representative cardiac information may be based on a plurality of electrode signals monitored, or measured, over a plurality of cardiac cycles or heart beats. The systems and methods may remove unqualified cardiac cycles, remove invalid electrode signals, remove inconsistent cardiac cycles, and removing uncorrelated cardiac cycles, and then generate representative cardiac information based on the remaining cardiac cycles and electrode signals.

33 Claims, 17 Drawing Sheets

(51) Int. Cl.
*A61B 5/341* (2021.01)
*A61N 1/365* (2006.01)

(56) References Cited

U.S. PATENT DOCUMENTS

| | | | |
|---|---|---|---|
| 7,286,866 | B2 | 10/2007 | Okerlund et al. |
| 7,308,297 | B2 | 12/2007 | Reddy et al. |
| 7,308,299 | B2 | 12/2007 | Burrell et al. |
| 7,321,677 | B2 | 1/2008 | Evron et al. |
| 7,346,381 | B2 | 3/2008 | Okerlund et al. |
| 7,454,248 | B2 | 11/2008 | Burrell et al. |
| 7,499,743 | B2 | 3/2009 | Vass et al. |
| 7,565,190 | B2 | 7/2009 | Okerlund et al. |
| 7,587,074 | B2 | 9/2009 | Zarkh et al. |
| 7,599,730 | B2 | 10/2009 | Hunter et al. |
| 7,613,500 | B2 | 11/2009 | Vass et al. |
| 7,684,863 | B2 | 3/2010 | Parikh et al. |
| 7,742,629 | B2 | 6/2010 | Zarkh et al. |
| 7,747,047 | B2 | 6/2010 | Okerlund et al. |
| 7,778,685 | B2 | 8/2010 | Evron et al. |
| 7,778,686 | B2 | 8/2010 | Vass et al. |
| 7,813,785 | B2 | 10/2010 | Okerlund et al. |
| 7,996,063 | B2 | 8/2011 | Vass et al. |
| 8,060,185 | B2 | 11/2011 | Hunter et al. |
| 8,180,428 | B2 | 5/2012 | Kaiser et al. |
| 8,401,616 | B2 | 3/2013 | Verard et al. |
| 8,731,642 | B2 | 5/2014 | Zarkh et al. |
| 8,861,830 | B2 | 10/2014 | Brada et al. |
| 8,972,228 | B2 | 3/2015 | Ghosh et al. |
| 9,320,446 | B2 | 4/2016 | Gillberg et al. |
| 9,486,151 | B2 | 11/2016 | Ghosh et al. |
| 9,510,763 | B2 | 12/2016 | Ghosh et al. |
| 9,737,223 | B2 | 8/2017 | Du et al. |
| 9,924,884 | B2 | 3/2018 | Ghosh et al. |
| 10,449,365 | B2 | 10/2019 | Ghosh |
| 2005/0008210 | A1 | 1/2005 | Evron et al. |
| 2006/0074285 | A1 | 4/2006 | Zarkh et al. |
| 2009/0009619 | A1 | 1/2009 | Takeda |
| 2012/0065528 | A1 | 3/2012 | Gill et al. |
| 2014/0323882 | A1 | 10/2014 | Ghosh et al. |
| 2014/0323892 | A1 | 10/2014 | Ghosh et al. |
| 2014/0371832 | A1 | 12/2014 | Ghosh |
| 2014/0371833 | A1 | 12/2014 | Ghosh et al. |
| 2015/0141765 | A1 | 5/2015 | Razavi et al. |
| 2017/0303840 | A1 | 10/2017 | Stadler et al. |
| 2018/0199843 | A1 | 7/2018 | Ghosh et al. |
| 2018/0263522 | A1 | 9/2018 | Ghosh et al. |
| 2019/0030331 | A1* | 1/2019 | Ghosh ............... A61N 1/3682 |
| 2019/0192029 | A1 | 6/2019 | Curtin et al. |
| 2019/0365271 | A1* | 12/2019 | Ghosh ............... A61B 5/318 |

OTHER PUBLICATIONS

International Preliminary Report on Patentability from PCT Application No. PCT/US2020/062616 dated Jun. 16, 2022, 7 pages.

Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, Feb. 2010, 21(2): 219-22.

Sperzel et al., "Intraoperative Characterization of Interventricular Mechanical Dyssynchrony Using Electroanatomic Mapping System—A Feasibility Study," Journal of Interventional Cardiac Electrophysiology, Nov. 2012, 35(2): 189-96.

Sweeney et al., "Analysis of Ventricular Activation Using Surface Electrocardiograma Predict Left Ventricular Reverse Volumetric Remodeling During Cardiac Resynchronization Therapy," Circulation, Feb. 9, 2010, 121(5): 626-34.

Van Deursen, et al., "Vectorcardiography as a Tool for Easy Optimization of Cardiac Resynchronization Therapy in Canine LBBB Hearts," Circulation Arrhythmia and Electrophysiology, Jun. 1, 2012, 5(3): 544-52.

Office Action issued in Europe for Application No. 20896241.5 dated Nov. 16, 2023 (9 pages).

* cited by examiner

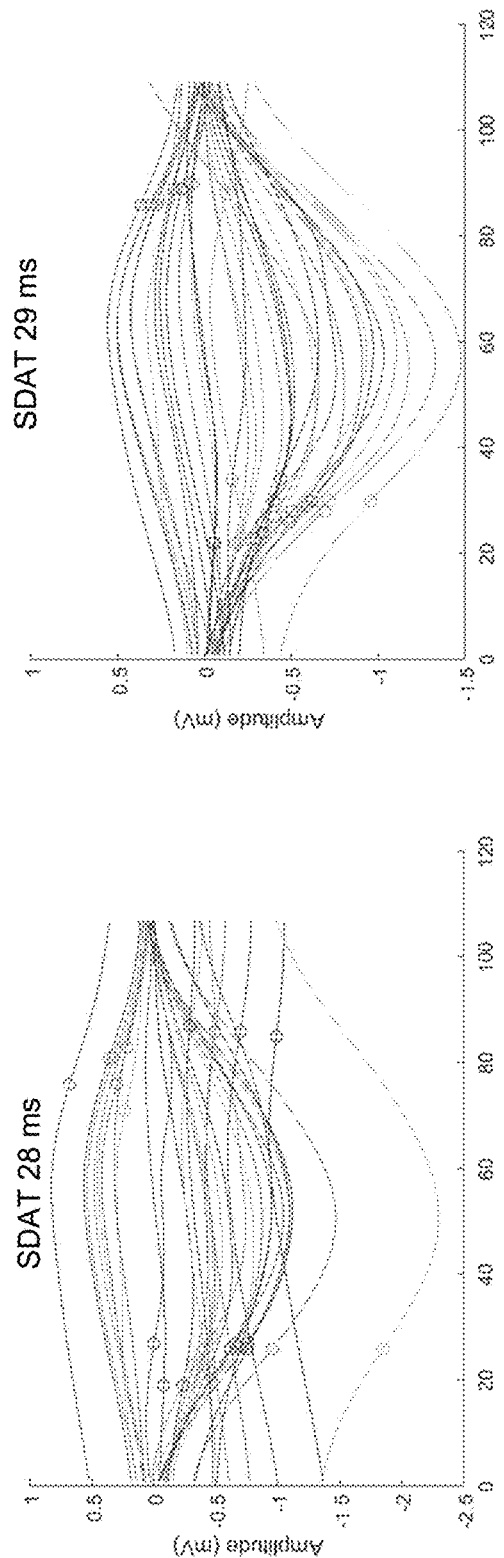
FIG. 12A
FIG. 12B
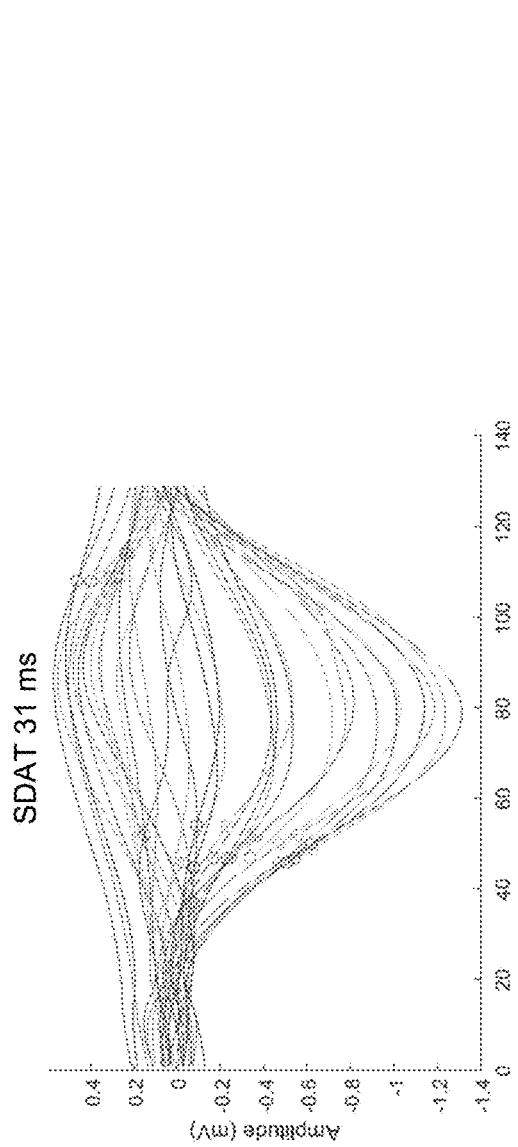
FIG. 12C

GENERATING REPRESENTATIVE CARDIAC INFORMATION

The present application claims the benefit of U.S. Provisional Application No. 62/942,555, filed Dec. 2, 2019, which is incorporated herein by reference in its entirety.

The disclosure herein relates to systems and methods for use in generating representative cardiac information using external electrode apparatus.

Implantable medical devices (IMDs), such as implantable pacemakers, cardioverters, defibrillators, or pacemaker-cardioverter-defibrillators, provide therapeutic electrical stimulation to the heart. IMDs may provide pacing to address bradycardia, or pacing or shocks in order to terminate tachyarrhythmia, such as tachycardia or fibrillation. In some cases, the medical device may sense intrinsic depolarizations of the heart, detect arrhythmia based on the intrinsic depolarizations (or absence thereof), and control delivery of electrical stimulation to the heart based on the intrinsic depolarizations.

IMDs may also provide cardiac resynchronization therapy (CRT), which is a form of pacing. CRT involves the delivery of pacing to the left ventricle, or both the left and right ventricles, as well as the atria. The timing and location of the delivery of pacing pulses to the ventricle(s) may be selected to improve the coordination and efficiency of ventricular contraction.

Systems for implanting medical devices may include workstations or other equipment in addition to the implantable medical device itself. In some cases, these other pieces of equipment assist the physician or other technician with placing the intracardiac leads at particular locations on or in the heart. In some cases, the equipment provides information to the physician about the electrical activity of the heart and the location of the intracardiac lead.

In some cases, the workstations or other equipment may include apparatus for obtaining electrocardiograms (ECG) via electrodes on the surface, or skin, of the patient. More specifically, the patient may have a plurality of electrodes on an ECG belt or vest that surrounds the torso of the patient. After the belt or vest has been secured to the torso, a physician can perform a series of tests to evaluate a patient's cardiac response. The data provided by the ECG electrodes placed on the body surface of the patient may be used for various therapeutic purposes (e.g., cardiac resynchronization therapy) including optimizing lead location, pacing parameters, etc. based on one or more metrics derived from the signals captured by the ECG electrodes. For example, electrical heterogeneity information (EHI) may be derived from electrical activation times computed from multiple electrodes on the body surface, and the EHI may be used to optimize lead location, pacing parameters, determine whether a patient qualifies for cardiac therapy, determine whether cardiac therapy would likely be effective for a patient, etc.

SUMMARY

The illustrative systems and methods described herein may be configured to assist a user (e.g., a physician) in evaluating and configuring cardiac therapy (e.g., cardiac therapy being performed on a patient during and/or after implantation of cardiac therapy apparatus). In one or more embodiments, the systems and methods may be described as being noninvasive. For example, in some embodiments, the systems and methods may not need, or include, implantable devices such as leads, probes, sensors, catheters, implantable electrodes, etc. to monitor, or acquire, a plurality of cardiac signals from tissue of the patient for use in evaluating and configuring the cardiac therapy being delivered to the patient. Instead, the systems and methods may use electrical measurements taken noninvasively using, e.g., a plurality of external electrodes attached to the skin of a patient about the patient's torso.

Some cardiac cycles, or heart beats, may not be representative, or reflective, of a patient's typical cardiac cycle or heartbeat. Calculation of electrical heterogeneity or dyssynchrony as well as other cardiac metrics from electrical activity monitored, or recorded, from external electrodes may have previously been based on a single cardiac cycle or beat. However, if that single cardiac cycle, or beat, is noisy or a non-representative of the patient's typical cardiac cycle, the data corresponding thereto may not reflect the true or accurate heterogeneity or dyssynchrony. Generally, the illustrative systems and methods utilizes data from multiple matching beats to formulate a more representative electrical dyssynchrony measure.

The illustrative systems and methods described herein may be utilized to determine representative cardiac information, such as representative electrical heterogeneity information (EHI), from a plurality of electrode signals measured, or monitored, over a plurality of cardiac cycles. For example, external electrode apparatus may be used to make a five second recording of ECG signal from multiple (e.g., about 40) electrodes and calculate a metric of electrical dyssynchrony. However, there may be beat-to-beat variations due to noise, physiology, and other factors. The illustrative systems and methods may automate one or more processes of deriving a representative metric of electrical dyssynchrony based on data from multiple beats that is more robust and accurate that previous processes or techniques. Additionally, the illustrative systems and methods may include performing a preliminary check of quality of each detected cardiac cycle, selecting cardiac cycles that passed the initial quality check, executing a phase-matched (e.g., based on peak) comparison of morphology of a standard deviation of signals of selected cardiac cycles, computing a representative measure based on electrical dyssynchrony from highly matched beats, and flagging recordings as noise in absence of at least two matching cardiac cycles.

It is to be understood that the term "cardiac cycle" and "heartbeat" are used herein interchangeably and may have a duration that includes a single cardiac depolarization (as opposed to multiple cardiac depolarizations). Further, it is to be understood that the illustrative systems and methods may generally be used to generate cardiac electrical activation times. The generation of such cardiac electrical activation times may generally utilize a fiducial point (e.g., greatest slope) within the QRS complex of a single cardiac cycle or heartbeat. It is be understood that, while the illustrative systems and methods described herein may remove and/or select cardiac cycles based on various criteria, such removal and/or selection may actually be referring to the removal and/or selection of QRS complexes corresponding to such cardiac cycles for use in generation of cardiac electrical activation times.

One illustrative system for use in cardiac evaluation may include electrode apparatus comprising a plurality of external electrodes to monitor electrical activity from tissue of a patient and a computing apparatus comprising processing circuitry and operably coupled to the electrode apparatus. The computing apparatus may be configured to monitor electrical activity using the plurality of external electrodes resulting in a plurality of electrode signals over a plurality of cardiac cycles, remove at least one unsatisfactory cardiac cycle from the plurality of cardiac cycles resulting in a representative set of cardiac cycles, and generate representative electrical heterogeneity information (EHI) based on the monitored electrical activity of the representative set of cardiac cycles.

One illustrative method for use in cardiac evaluation may include monitoring electrical activity using a plurality of external electrodes from tissue of a patient resulting in a plurality of electrode signals over a plurality of cardiac cycles, removing at least one unsatisfactory cardiac cycle from the plurality of cardiac cycles resulting in a representative set of cardiac cycles, and generating representative electrical heterogeneity information (EHI) based on the monitored electrical activity of the representative set of cardiac cycles.

One illustrative system for use in cardiac evaluation may include electrode apparatus comprising a plurality of external electrodes to monitor electrical activity from tissue of a patient and a computing apparatus comprising processing circuitry and operably coupled to the electrode apparatus. The computing apparatus may be configured to monitor electrical activity using the plurality of external electrodes resulting in a plurality of electrode signals over a plurality of cardiac cycles and remove invalid signals from the plurality of electrode signals over the plurality of cardiac cycles resulting in a plurality of valid electrode signals over the plurality of cardiac cycles. The computing apparatus may be further configured to remove unqualified cardiac cycles from the plurality of cardiac cycles based on the plurality of valid electrode signals over the plurality of cardiac cycles resulting in a qualified set of cardiac cycles, remove uncorrelated cardiac cycles from the qualified set of cardiac cycles based on the plurality of valid electrode signals over the qualified set of cardiac cycles resulting in a correlated set of cardiac cycles, and remove inconsistent cardiac cycles from the correlated set of cardiac cycles based on the plurality of valid electrode signals over the correlated set of cardiac cycles resulting in a representative set of cardiac cycles.

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIGS. 12A-12C depict a plurality of electrode signals of a representative set of cardiac cycles identified in FIG. 11.

DETAILED DESCRIPTION OF ILLUSTRATIVE EMBODIMENTS

Figure 1:
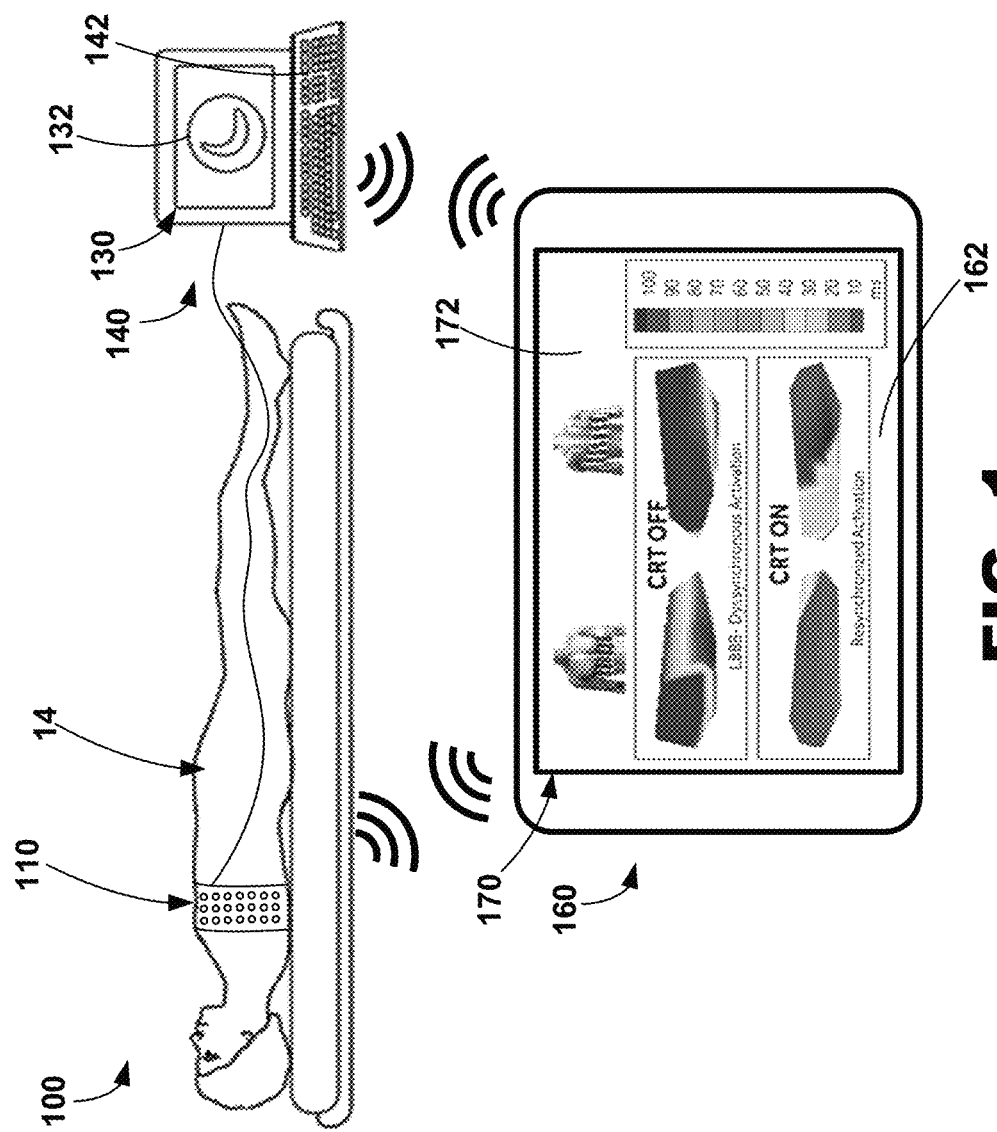
FIG. 1 is a diagram of an illustrative system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Illustrative systems and methods shall be described with reference to FIGS. 1-15. It will be apparent to one skilled in the art that elements or processes from one embodiment may be used in combination with elements or processes of the other embodiments, and that the possible embodiments of such systems, methods, and devices using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

A plurality of electrocardiogram (ECG) signals (e.g., torso-surface potentials) may be measured, or monitored, using a plurality of external electrodes positioned about the surface, or skin, of a patient. The ECG signals may be used to evaluate and configure cardiac therapy such as, e.g., cardiac therapy provide by an implantable medical device performing cardiac resynchronization therapy (CRT). As described herein, the ECG signals may be gathered or obtained noninvasively since, e.g., implantable electrodes may not be used to measure the ECG signals. Further, the ECG signals may be used to determine cardiac electrical activation times, which may be used to generate various metrics (e.g., electrical heterogeneity information) that may be used by a user (e.g., physician) to optimize one or more settings, or parameters, of cardiac therapy (e.g., pacing therapy) such as CRT.

Various illustrative systems, methods, and graphical user interfaces may be configured to use electrode apparatus including external electrodes, display apparatus, and computing apparatus to noninvasively assist a user (e.g., a physician) in the evaluation of cardiac health and/or the configuration (e.g., optimization) of cardiac therapy. An illustrative system 100 including electrode apparatus 110, computing apparatus 140, and a remote computing device 160 is depicted in FIG. 1.

The electrode apparatus 110 as shown includes a plurality of electrodes incorporated, or included, within a band wrapped around the chest, or torso, of a patient 14. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Illustrative electrode apparatus may be described in U.S. Pat. No. 9,320,446 entitled "Bioelectric Sensor Device and Methods" filed Mar. 27, 2014 and issued on Mar. 26, 2016, which is incorporated herein by reference in its entirety. Further, illustrative electrode apparatus 110 will be described in more detail in reference to FIGS. 2-3.

Although not described herein, the illustrative system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the illustrative systems, methods, and interfaces described herein may further use imaging apparatus to provide noninvasive assistance to a user (e.g., a physician) to locate, or place, one or more pacing electrodes proximate the patient's heart in conjunction with the configuration of cardiac therapy.

For example, the illustrative systems and methods may provide image guided navigation that may be used to navigate leads including electrodes, leadless electrodes, wireless electrodes, catheters, etc., within the patient's body while also providing noninvasive cardiac therapy configuration including determining an effective, or optimal, pre-excitation intervals such as A-V and V-V intervals, etc. Illustrative systems and methods that use imaging apparatus and/or electrode apparatus may be described in U.S. Pat. No. 9,877,789 to Ghosh issued on Jan. 30, 2018, U.S. Pat. No. 10,251,555 to Ghosh et al. issued on Apr. 9, 2019, U.S. Pat. No. 9,924,884 to Ghosh et al. issued on Mar. 27, 2018, U.S. Pat. No. 10,064,567 to Ghosh et al. issued on Sep. 4, 2018, each of which is incorporated herein by reference in its entirety.

Illustrative imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MM), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative Mill, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. An exemplary system that employs ultrasound can be found in U.S. Pat. No. 11,253,178 entitled NONINVASIVE ASSESSMENT OF CARDIAC RESYNCHRONIZATION THERAPY to Stadler et al. issued on Feb. 22, 2022, incorporated by reference in its entirety. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate implantable apparatus to target locations within the heart or other areas of interest.

Systems and/or imaging apparatus that may be used in conjunction with the illustrative systems and method described herein are described in abandoned U.S. Pat. App. Pub. No. 2005/0008210 to Evron et al. published on Jan. 13, 2005, abandoned U.S. Pat. App. Pub. No. 2006/0074285 to Zarkh et al. published on Apr. 6, 2006, U.S. Pat. No. 8,731,642 to Zarkh et al. issued on May 20, 2014, U.S. Pat. No. 8,861,830 to Brada et al. issued on Oct. 14, 2014, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The computing apparatus 140 and the remote computing device 160 may each include display apparatus 130, 170, respectively, that may be configured to display and analyze data such as, e.g., electrical signals (e.g., electrocardiogram data), electrical activation times, electrical heterogeneity information, etc. For example, one cardiac cycle, or one heartbeat, of a plurality of cardiac cycles, or heartbeats, represented by the electrical signals collected or monitored by the electrode apparatus 110 may be analyzed and evaluated for one or more metrics including activation times and electrical heterogeneity information that may be pertinent to the therapeutic nature of one or more parameters related to cardiac therapy such as, e.g., pacing parameters, lead location, etc. More specifically, for example, the QRS complex of a single cardiac cycle may be evaluated for one or more metrics such as, e.g., QRS onset, QRS offset, QRS peak, electrical heterogeneity information (EHI), electrical activation times referenced to earliest activation time, left ventricular or thoracic standard deviation of electrical activation times (LVED), standard deviation of activation times (SDAT), average left ventricular or thoracic surrogate electrical activation times (LVAT), QRS duration (e.g., interval between QRS onset to QRS offset), difference between average left surrogate and average right surrogate activation times, relative or absolute QRS morphology, difference between a higher percentile and a lower percentile of activation times (higher percentile may be 90%, 80%, 75%, 70%, etc. and lower percentile may be 10%, 15%, 20%, 25% and 30%, etc.), other statistical measures of central tendency (e.g., median or mode), dispersion (e.g., mean deviation, standard deviation, variance, interquartile deviations, range), etc. Further, each of the one or more metrics may be location specific. For example, some metrics may be computed from signals recorded, or monitored, from electrodes positioned about a selected area of the patient such as, e.g., the left side of the patient, the right side of the patient, etc.

In at least one embodiment, one or both of the computing apparatus 140 and the remote computing device 160 may be a server, a personal computer, a tablet computer, a mobile device, and a cellular telephone. The computing apparatus 140 may be configured to receive input from input apparatus 142 (e.g., a keyboard) and transmit output to the display apparatus 130, and the remote computing device 160 may be configured to receive input from input apparatus 162 (e.g., a touchscreen) and transmit output to the display apparatus 170. One or both of the computing apparatus 140 and the remote computing device 160 may include data storage that may allow for access to processing programs or routines and/or one or more other types of data, e.g., for analyzing a plurality of electrical signals captured by the electrode apparatus 110, for determining QRS onsets, QRS offsets, medians, modes, averages, peaks or maximum values, valleys or minimum values, for determining electrical activation times, for driving a graphical user interface configured to noninvasively assist a user in configuring one or more pacing parameters, or settings, such as, e.g., pacing rate, ventricular pacing rate, A-V interval, V-V interval, pacing pulse width, pacing vector, multipoint pacing vector (e.g., left ventricular vector quad lead), pacing voltage, pacing configuration (e.g., biventricular pacing, right ventricle only pacing, left ventricle only pacing, etc.), and arrhythmia detection and treatment, rate adaptive settings and performance, etc.

The computing apparatus 140 may be operatively coupled to the input apparatus 142 and the display apparatus 130 to, e.g., transmit data to and from each of the input apparatus 142 and the display apparatus 130, and the remote computing device 160 may be operatively coupled to the input apparatus 162 and the display apparatus 170 to, e.g., transmit data to and from each of the input apparatus 162 and the display apparatus 170. For example, the computing apparatus 140 and the remote computing device 160 may be electrically coupled to the input apparatus 142, 162 and the display apparatus 130, 170 using, e.g., analog electrical connections, digital electrical connections, wireless connections, bus-based connections, network-based connections, internet-based connections, etc. As described further herein, a user may provide input to the input apparatus 142, 162 to view and/or select one or more pieces of configuration information related to the cardiac therapy delivered by cardiac therapy apparatus such as, e.g., an implantable medical device.

Although as depicted the input apparatus 142 is a keyboard and the input apparatus 162 is a touchscreen, it is to be understood that the input apparatus 142, 162 may include any apparatus capable of providing input to the computing apparatus 140 and the computing device 160 to perform the functionality, methods, and/or logic described herein. For example, the input apparatus 142, 162 may include a keyboard, a mouse, a trackball, a touchscreen (e.g., capacitive touchscreen, a resistive touchscreen, a multi-touch touchscreen, etc.), etc. Likewise, the display apparatus 130, 170 may include any apparatus capable of displaying information to a user, such as a graphical user interface 132, 172 including electrode status information, graphical maps of electrical activation, a plurality of signals for the external electrodes over one or more heartbeats, QRS complexes, various cardiac therapy scenario selection regions, various rankings of cardiac therapy scenarios, various pacing parameters, electrical heterogeneity information (EHI), textual instructions, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130, 170 may include a liquid crystal display, an organic light-emitting diode screen, a touchscreen, a cathode ray tube display, etc.

The processing programs or routines stored and/or executed by the computing apparatus 140 and the remote computing device 160 may include programs or routines for computational mathematics, matrix mathematics, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing used to implement one or more illustrative methods and/or processes described herein. Data stored and/or used by the computing apparatus 140 and the remote computing device 160 may include, for example, electrical signal/waveform data from the electrode apparatus 110 (e.g., a plurality of QRS complexes), electrical activation times from the electrode apparatus 110, cardiac sound/signal/waveform data from acoustic sensors, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, electrical heterogeneity information, etc.), or any other data that may be used for carrying out the one and/or more processes or methods described herein.

In one or more embodiments, the illustrative systems, methods, and interfaces may be implemented using one or more computer programs executed on programmable computers, such as computers that include, for example, processing capabilities, data storage (e.g., volatile or nonvolatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the illustrative systems, methods, and interfaces may be implemented using a computer readable storage medium, configured with a computer program, where the storage medium so configured causes the computer to operate in a specific and predefined manner to perform functions described herein. Further, in at least one embodiment, the illustrative systems, methods, and interfaces may be described as being implemented by logic (e.g., object code) encoded in one or more non-transitory media that includes code for execution and, when executed by a processor or processing circuitry, is operable to perform operations such as the methods, processes, and/or functionality described herein.

The computing apparatus 140 and the remote computing device 160 may be, for example, any fixed or mobile computer system (e.g., a controller, a microcontroller, a personal computer, minicomputer, tablet computer, etc.). The exact configurations of the computing apparatus 140 and the remote computing device 160 are not limiting, and essentially any device capable of providing suitable computing capabilities and control capabilities (e.g., signal analysis, mathematical functions such as medians, modes, averages, maximum value determination, minimum value determination, slope determination, minimum slope determination, maximum slope determination, graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by the computing apparatus 140 and the remote computing device 160 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes, or programs (e.g., the functionality provided by such systems, processes, or programs) described herein.

Figure 2:
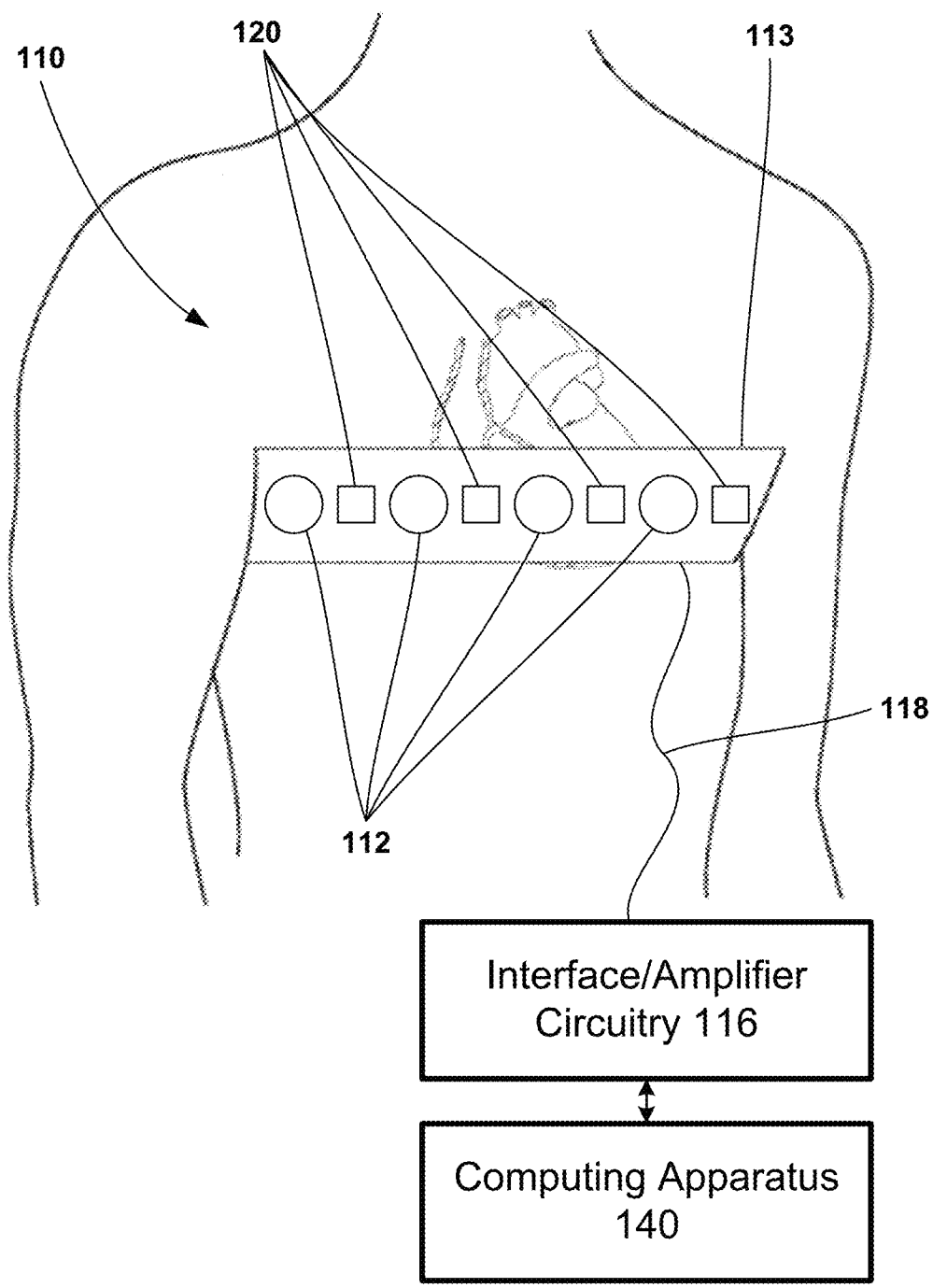
FIGS. 2-3 are diagrams of illustrative external electrode apparatus for measuring torso-surface potentials.

The illustrative electrode apparatus 110 may be configured to measure body-surface potentials of a patient 14 and, more particularly, torso-surface potentials of a patient 14. As shown in FIG. 2, the illustrative electrode apparatus 110 may include a set, or array, of external electrodes 112, a strap 113, and interface/amplifier circuitry 116. The electrodes 112 may be attached, or coupled, to the strap 113 and the strap 113 may be configured to be wrapped around the torso of a patient 14 such that the electrodes 112 surround the patient's heart. As further illustrated, the electrodes 112 may be positioned around the circumference of a patient 14, including the posterior, lateral, posterolateral, anterolateral, and anterior locations of the torso of a patient 14.

The illustrative electrode apparatus 110 may be further configured to measure, or monitor, sounds from at least one or both the patient 14. As shown in FIG. 2, the illustrative electrode apparatus 110 may include a set, or array, of acoustic sensors 120 attached, or coupled, to the strap 113. The strap 113 may be configured to be wrapped around the torso of a patient 14 such that the acoustic sensors 120 surround the patient's heart. As further illustrated, the acoustic sensors 120 may be positioned around the circumference of a patient 14, including the posterior, lateral, posterolateral, anterolateral, and anterior locations of the torso of a patient 14.

Further, the electrodes 112 and the acoustic sensors 120 may be electrically connected to interface/amplifier circuitry 116 via wired connection 118. The interface/amplifier circuitry 116 may be configured to amplify the signals from the electrodes 112 and the acoustic sensors 120 and provide the signals to one or both of the computing apparatus 140 and the remote computing device 160. Other illustrative systems may use a wireless connection to transmit the signals sensed by electrodes 112 and the acoustic sensors 120 to the interface/amplifier circuitry 116 and, in turn, to one or both of the computing apparatus 140 and the remote computing device 160, e.g., as channels of data. In one or more embodiments, the interface/amplifier circuitry 116 may be electrically coupled to the computing apparatus 140 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112 and the acoustic sensors 120. In some examples, the strap 113 may include an elastic band, strip of tape, or cloth. Further, in some examples, the strap 113 may be part of, or integrated with, a piece of clothing such as, e.g., a t-shirt. In other examples, the electrodes 112 and the acoustic sensors 120 may be placed individually on the torso of a patient 14. Further, in other examples, one or both of the electrodes 112 (e.g., arranged in an array) and the acoustic sensors 120 (e.g., also arranged in an array) may be part of, or located within, patches, vests, and/or other manners of securing the electrodes 112 and the acoustic sensors 120 to the torso of the patient 14. Still further, in other examples, one or both of the electrodes 112 and the acoustic sensors 120 may be part of, or located within, two sections of material or two patches. One of the two patches may be located on the anterior side of the torso of the patient 14 (to, e.g., monitor electrical signals representative of the anterior side of the patient's heart, measure surrogate cardiac electrical activation times representative of the anterior side of the patient's heart, monitor or measure sounds of the anterior side of the patient, etc.) and the other patch may be located on the posterior side of the torso of the patient 14 (to, e.g., monitor electrical signals representative of the posterior side of the patient's heart, measure surrogate cardiac electrical activation times representative of the posterior side of the patient's heart, monitor or measure sounds of the posterior side of the patient, etc.). And still further, in other examples, one or both of the electrodes 112 and the acoustic sensors 120 may be arranged in a top row and bottom row that extend from the anterior side of the patient 14 across the left side of the patient 14 to the posterior side of the patient 14. Yet still further, in other examples, one or both of the electrodes 112 and the acoustic sensors 120 may be arranged in a curve around the armpit area and may have an electrode/sensor-density that less dense on the right thorax that the other remaining areas.

The electrodes 112 may be configured to surround the heart of the patient 14 and record, or monitor, the electrical signals associated with the depolarization and repolarization of the heart after the signals have propagated through the torso of a patient 14. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing.

In some examples, there may be about 12 to about 50 electrodes 112 and about 12 to about 50 acoustic sensors 120 spatially distributed around the torso of a patient. Other configurations may have more or fewer electrodes 112 and more or fewer acoustic sensors 120. It is to be understood that the electrodes 112 and acoustic sensors 120 may not be arranged or distributed in an array extending all the way around or completely around the patient 14. Instead, the electrodes 112 and acoustic sensors 120 may be arranged in an array that extends only part of the way or partially around the patient 14. For example, the electrodes 112 and acoustic sensors 120 may be distributed on the anterior, posterior, and left sides of the patient with less or no electrodes and acoustic sensors proximate the right side (including posterior and anterior regions of the right side of the patient).

The computing apparatus 140 may record and analyze the torso-surface potential signals sensed by electrodes 112 and the sound signals sensed by the acoustic sensors 120, which are amplified/conditioned by the interface/amplifier circuitry 116. The computing apparatus 140 may be configured to analyze the electrical signals from the electrodes 112 to provide electrocardiogram (ECG) signals, information, or data from the patient's heart as will be further described herein. The computing apparatus 140 may be configured to analyze the electrical signals from the acoustic sensors 120 to provide sound signals, information, or data from the patient's body and/or devices implanted therein (such as a left ventricular assist device).

Additionally, the computing apparatus 140 and the remote computing device 160 may be configured to provide graphical user interfaces 132, 172 depicting various information related to the electrode apparatus 110 and the data gathered, or sensed, using the electrode apparatus 110. For example, the graphical user interfaces 132, 172 may depict ECGs including QRS complexes obtained using the electrode apparatus 110 and sound data including sound waves obtained using the acoustic sensors 120 as well as other information related thereto. Illustrative systems and methods may noninvasively use the electrical information collected using the electrode apparatus 110 and the sound information collected using the acoustic sensors 120 to evaluate a patient's cardiac health and to evaluate and configure cardiac therapy being delivered to the patient.

Further, the electrode apparatus 110 may further include reference electrodes and/or drive electrodes to be, e.g. positioned about the lower torso of the patient 14, that may be further used by the system 100. For example, the electrode apparatus 110 may include three reference electrodes, and the signals from the three reference electrodes may be combined to provide a reference signal. Further, the electrode apparatus 110 may use of three caudal reference electrodes (e.g., instead of standard references used in a Wilson Central Terminal) to get a "true" unipolar signal with less noise from averaging three caudally located reference signals.

Figure 3:
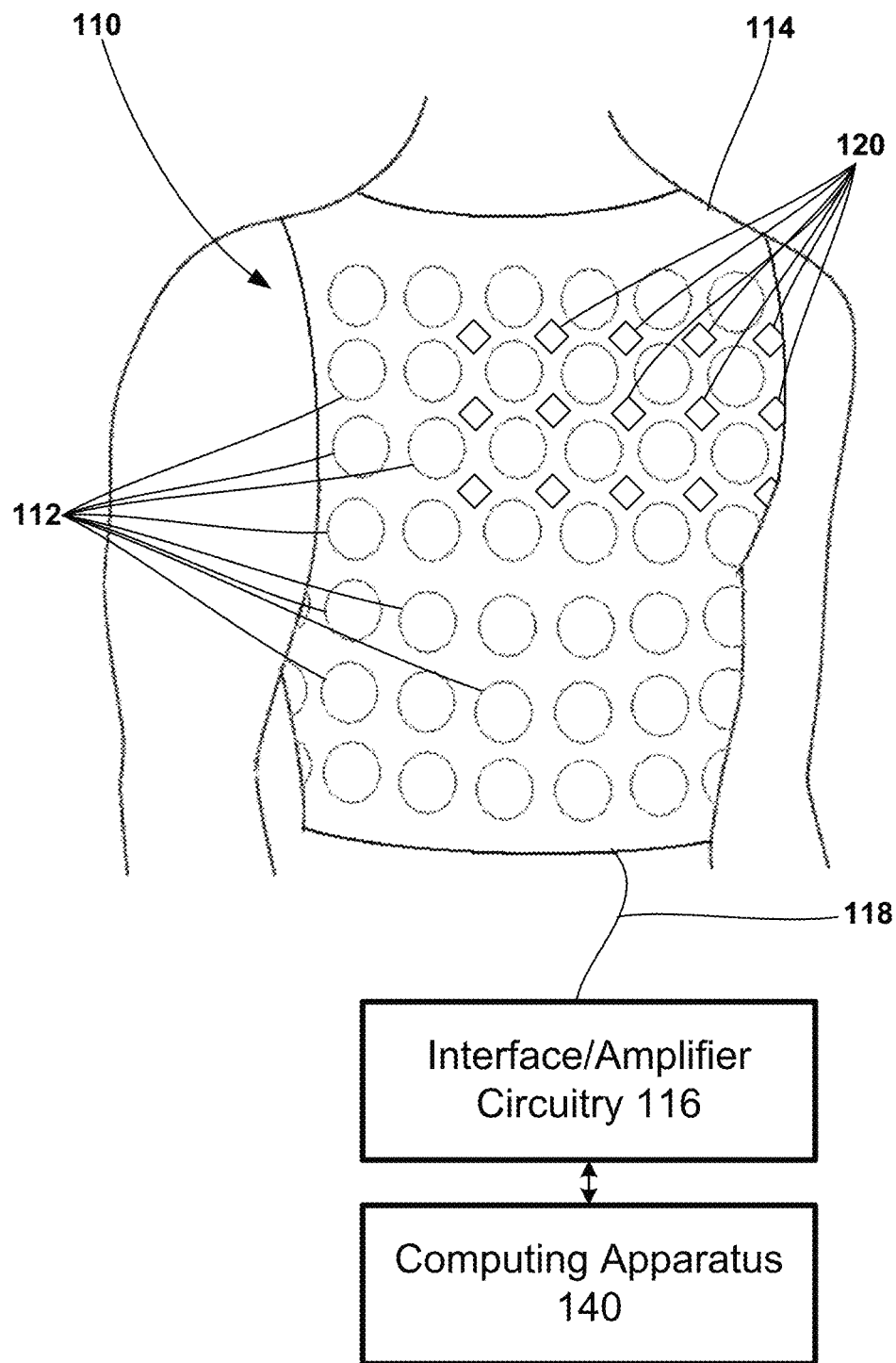

FIG. 3 illustrates another illustrative electrode apparatus 110 that includes a plurality of electrodes 112 configured to surround the heart of the patient 14 and record, or monitor, the electrical signals associated with the depolarization and repolarization of the heart after the signals have propagated through the torso of the patient 14 and a plurality of acoustic sensors 120 configured to surround the heart of the patient 14 and record, or monitor, the sound signals associated with the heart after the signals have propagated through the torso of the patient 14. The electrode apparatus 110 may include a vest 114 upon which the plurality of electrodes 112 and the plurality of acoustic sensors 120 may be attached, or to which the electrodes 112 and the acoustic sensors 120 may be coupled. In at least one embodiment, the plurality, or array, of electrodes 112 may be used to collect electrical information such as, e.g., surrogate electrical activation times. Similar to the electrode apparatus 110 of FIG. 2, the electrode apparatus 110 of FIG. 3 may include interface/amplifier circuitry 116 electrically coupled to each of the electrodes 112 and the acoustic sensors 120 through a wired connection 118 and be configured to transmit signals from the electrodes 112 and the acoustic sensors 120 to computing apparatus 140. As illustrated, the electrodes 112 and the acoustic sensors 120 may be distributed over the torso of a patient 14, including, for example, the posterior, lateral, posterolateral, anterolateral, and anterior locations of the torso of a patient 14.

The vest 114 may be formed of fabric with the electrodes 112 and the acoustic sensors 120 attached to the fabric. The vest 114 may be configured to maintain the position and spacing of electrodes 112 and the acoustic sensors 120 on the torso of the patient 14. Further, the vest 114 may be marked to assist in determining the location of the electrodes 112 and the acoustic sensors 120 on the surface of the torso of the patient 14. In some examples, there may be about 25 to about 256 electrodes 112 and about 25 to about 256 acoustic sensors 120 distributed around the torso of the patient 14, though other configurations may have more or fewer electrodes 112 and more or fewer acoustic sensors 120.

The illustrative systems and methods may be used to provide noninvasive assistance to a user in the evaluation of a patient's cardiac health and/or evaluation and configuration of cardiac therapy being presently delivered to the patient (e.g., by an implantable medical device delivering pacing therapy, by a LVAD, etc.). Further, it is to be understood that the computing apparatus 140 and the remote computing device 160 may be operatively coupled to each other in a plurality of different ways so as to perform, or execute, the functionality described herein. For example, in the embodiment depicted, the computing device 140 may be wireless operably coupled to the remote computing device 160 as depicted by the wireless signal lines emanating therebetween. Additionally, as opposed to wireless connections, one or more of the computing apparatus 140 and the remoting computing device 160 may be operably coupled through one or wired electrical connections.

Figure 4:
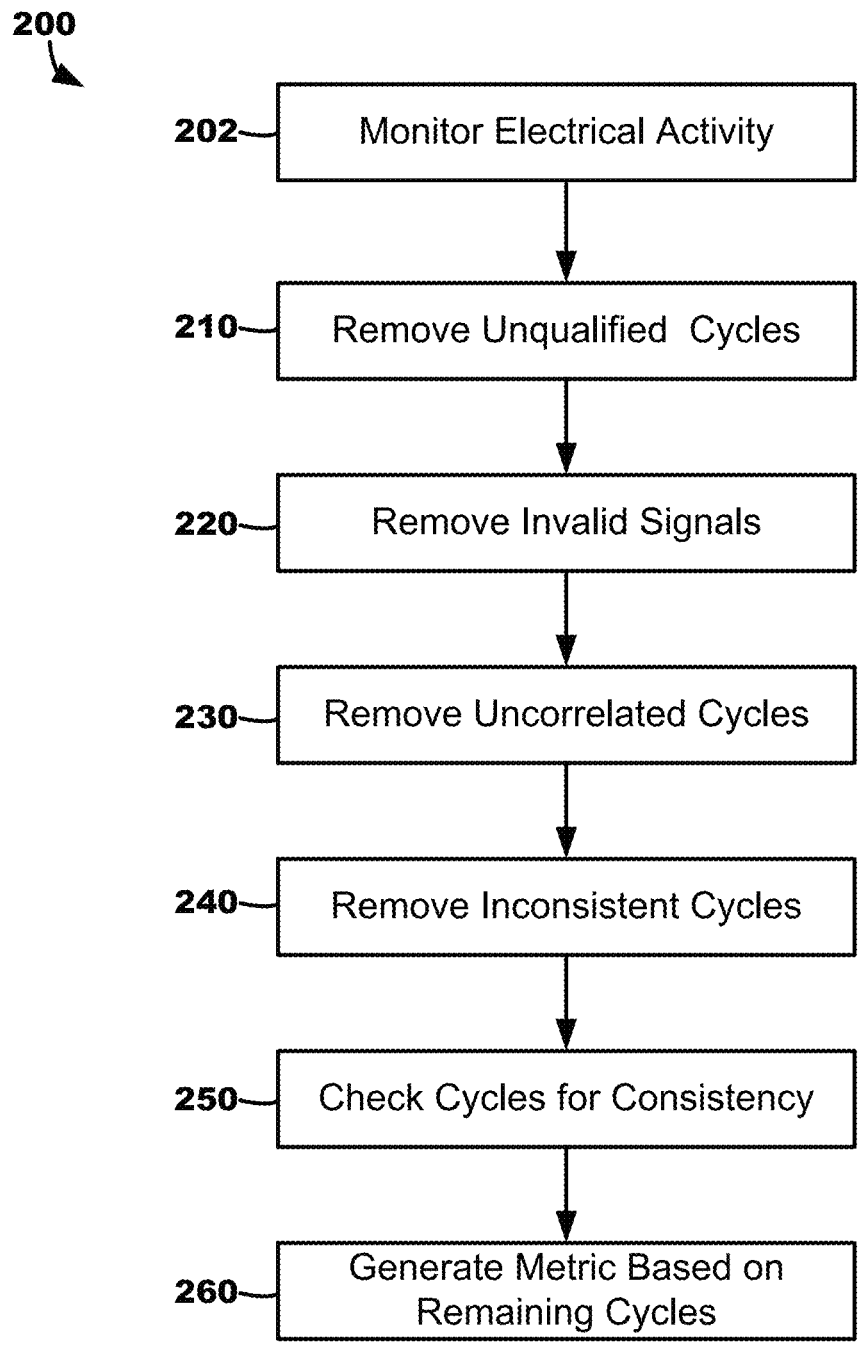
FIG. 4 is a block diagram of an illustrative method of generating representative cardiac information based on electrode signals monitored over a plurality of cardiac cycles.

An illustrative method 200 of generation of representative cardiac information, such as, e.g., electrical heterogeneity information (EHI), based on electrode signals monitored over a plurality of cardiac cycles is depicted in FIG. 4. The method 200 includes monitoring, or measuring, electrical activity 202 of the patient using a plurality of external electrodes such as found on electrode apparatus 110 described herein as described herein with respect to FIGS. 1-3. For example, the plurality of external electrodes may be part of, or incorporated into, a vest or band that is located about a patient's torso. More specifically, the plurality of electrodes may be described as being surface electrodes positioned in an array configured to be located proximate the skin of the torso of a patient.

The electrical activity may be monitored 202 for, or over, a plurality of cardiac cycles or heartbeats. For example, the electrical activity may be monitored 202 for two or more cardiac cycles, three or more cardiac cycles, five or more cardiac cycles, ten or more cardiac cycles, etc. In at least one embodiment, the electrical activity may be monitored 202 for six cardiac cycles. Further, the electrical activity 202 may be monitored for a selected period of time such as, e.g., three or more seconds, five seconds or more seconds, ten or more seconds, etc. In at least one embodiment, the electrical activity may be monitored 202 for five seconds. As described herein, some of the electrode signals as well as some of the cardiac cycles may be irregular or have other undesirable characteristics or features (e.g., noise, etc.) that makes the electrode signals or cardiac cycles undesirable for further analysis with respect to a patient's cardiac health or cardiac therapy being delivered to the patient.

Monitoring, or measuring, electrical activity 202 over a plurality of cardiac cycles using a plurality of external electrodes will result in a plurality of electrode signals over a plurality of cardiac cycles. In essence, each electrode signal will have been measured using a different external electrode of the plurality of external electrodes. Thus, each electrode signal corresponds to a single external electrode that is located in a different location about the patient's torso than the remainder of the external electrodes.

The remainder of the illustrative method 200 includes various processes configured to provide, or generate, representative cardiac information such as, e.g., representative electrical heterogeneity information (EHI) based on the plurality of electrode signals monitored over a plurality of cardiac cycles from process 202. Although the proceeds, or steps, of method 200 are depicted in a particular order, it is to be understood that such particular order is only one illustrative embodiment and that other orders, or sequences, of such processes is contemplated herein.

The illustrative method 200 may include removing unqualified cardiac cycles 210. The removal of unqualified cardiac cycles 210 may be based on various criteria of, or with respect to, the plurality of electrode signals. In essence, it may be described that removing unqualified cardiac cycles 210 is intended to ensure that only reasonably-good cardiac cycles, or beats, are utilized to generate representative cardiac information. Thus, representative cardiac information may be generated based on electrical activity monitored over cardiac cycles that are determined to be reasonably-good or qualified.

Figure 5:
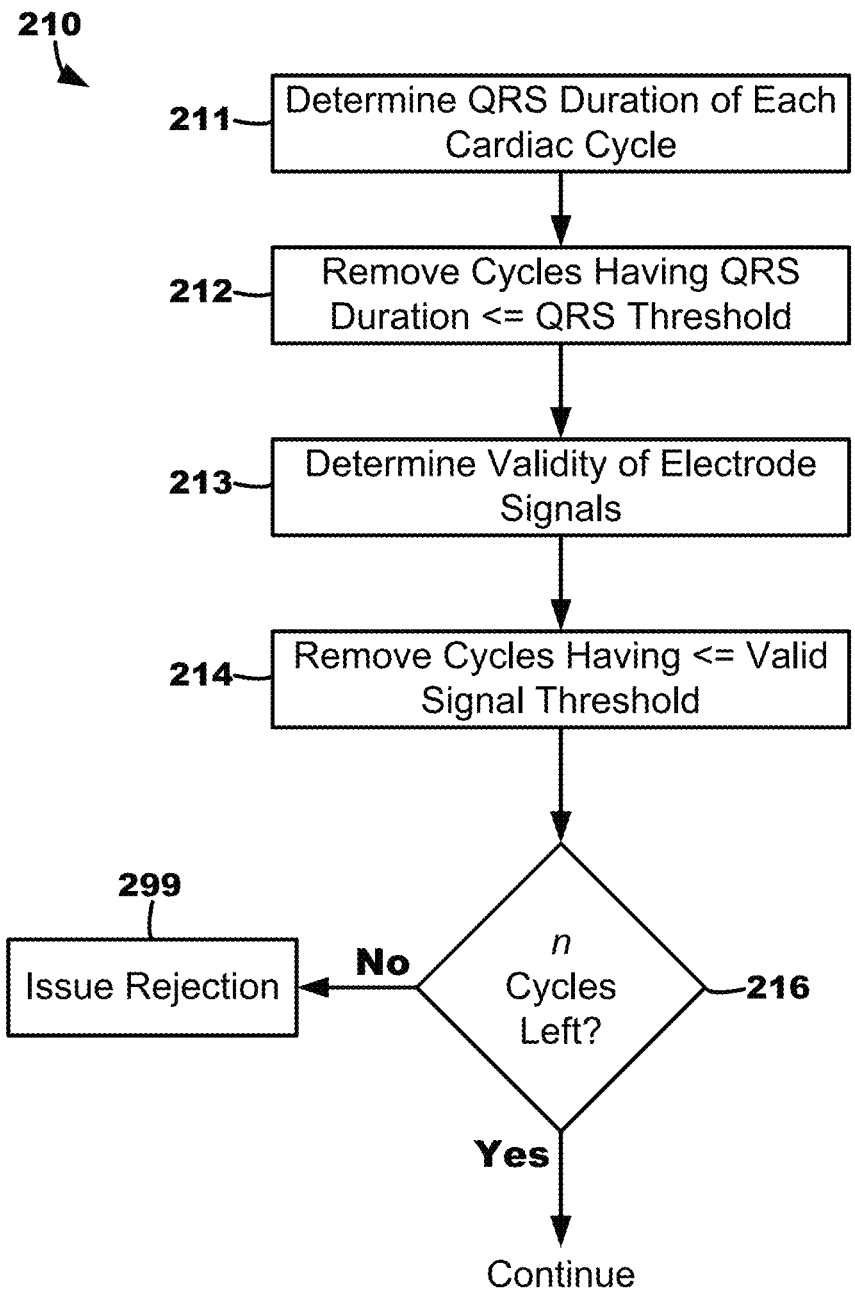
FIG. 5 is an illustrative method of removing unqualified cardiac cycles.

One illustrative method of removing unqualified cardiac cycles 210 is depicted in FIG. 5. As shown, the QRS duration, or the difference between QRS onset and the QRS offset, of each cardiac cycle may be determined 211 based on the plurality of electrode signals. Illustrative QRS duration, as well as QRS onset and offset, determination, or measurement, may be described in U.S. Pat. App. Pub. No. 2018/0263522 A1 entitled "QRS Offset and Onset Determination published on Sep. 20, 2018, U.S. Pat. No. 10,449,365 entitled "Determining Onsets and Offsets of Cardiac Depolarization and Repolarization Waves" issued on Oct. 22, 2019, and U.S. Pat. No. 9,737,223 entitled "Determining Onset of Cardiac Depolarization and Repolarization Waves for Signal Processing" issued on Aug. 22, 2018, each of which are incorporated by reference in their entireties. Then, any cardiac cycles having a QRS duration less than or equal to a QRS duration threshold value may be removed 212. The QRS duration threshold may be between about 90 milliseconds (ms) and about 300 ms. In at least one embodiment, the QRS duration threshold is 70 ms.

It is be understood herein that when a cardiac cycle is removed that the portion of the plurality of electrode signals covering, or monitored during, the removed cardiac cycle will not be utilized further with the method 200. In other words, the cardiac cycles within the plurality of electrode signals will not be considered further if such cardiac cycles are removed. When a cardiac cycle is removed using process 212 as well as other processes described herein, such cardiac cycle may be considered removed from a set of cardiac cycles that will be used to generate representative cardiac information. In other words, the processes described herein may start with a plurality of cardiac cycles, and some of the cardiac cycles may be removed for various reasons resulting in a representative set of cardiac cycles. Thus, the representative set of cardiac cycles includes cardiac cycles that have not been removed for being unqualified, uncorrelated, inconsistent, etc. as further described herein.

Additionally, the validity of each electrode signal may be determined 213. For example, the validity of each electrode signal may be determined, or measured, by monitoring portions of each signal and comparing such portions to each other determine the effectiveness or validity of the signal. Further, for example, the validity of each electrode signal may be determined, or measured, by monitoring portions of each signal and comparing such portions to time-corresponding portions of other electrode signals to determine the effectiveness or validity of the signal. In one embodiment, an electrode signal may be expected to be in a window from QRS onset to QRS offset that mathematically correlates to at least one of its neighbor electrode signals. In another embodiment the electrode signal in one QRS window may be correlated to the same electrode signals in other QRS window. In one or more embodiments, electrode signal validity determination may be described in U.S. Pat. No. 9,924,884 entitled "Systems, methods, and interfaces for identifying effective electrodes" issued on Mar. 27, 2018, which is incorporated by reference herein in its entirety.

Then, any cardiac cycle having an amount or number of valid electrode signals less than a valid electrode signal threshold may be removed from further consideration within the representative set of cardiac cycles 214. The valid electrode signal threshold may be a numerical value between about 15 and about 35. In one embodiment, the valid electrode is 25. The valid electrode signal threshold may be a percentage of the total amount of electrodes and may be between about 50% and about 90%. In one embodiment, the valid electrode threshold is 60% of the total amount of electrodes.

The method, or process, 210 may then check to see if a selected number, n, cardiac cycles remain 216 after the removal processes 212, 214. The selected number, n, of cardiac cycles may be between 1 cardiac cycle and 15 cardiac cycles. In at least one embodiment, the selected number, n, of cardiac cycles is 2 cardiac cycles. If n cycles remain after removal, then the method, or process, may continue 210. If n cycles do not remain after removal, then the method, or process, may issue a rejection 299.

After the issuance of a rejection, a user or operator may be instructed to restart the method 200 and recollect data using the plurality of electrodes in process 202. For example, if n is three and less than three cardiac cycles remain in the representative set of cardiac cycles after removing at least one cardiac cycle in processes 212, 214, then a data rejection may be issued 299.

The illustrative method 200 may further include removing invalid cardiac signals 220. The removal of invalid cardiac cycles 220 may be based on various criteria of, or with respect to, the plurality of electrode signals. In essence, it may be described that electrode signals may be evaluated beat-to-beat and it may be determined whether each electrode signal is valid across a selected number of cardiac cycles (e.g., all cardiac cycles recorded or monitored, less than all cardiac cycles recorded or monitored, more than about half of all cardiac cycles recorded or monitored, etc.). Invalid electrode signals 220 may be removed to provide that only cardiac cycles, or beats, recorded using valid electrode signals are utilized to generate representative cardiac information. Thus, representative cardiac information may then be generated based on electrical activity monitored using valid electrode signals. It is be understood herein that when an electrode signal is removed that such electrode signal will not be utilized further with the method 200. In other words, the removed electrode signal will not be considered further in the generation of representative cardiac information.

Figure 6:
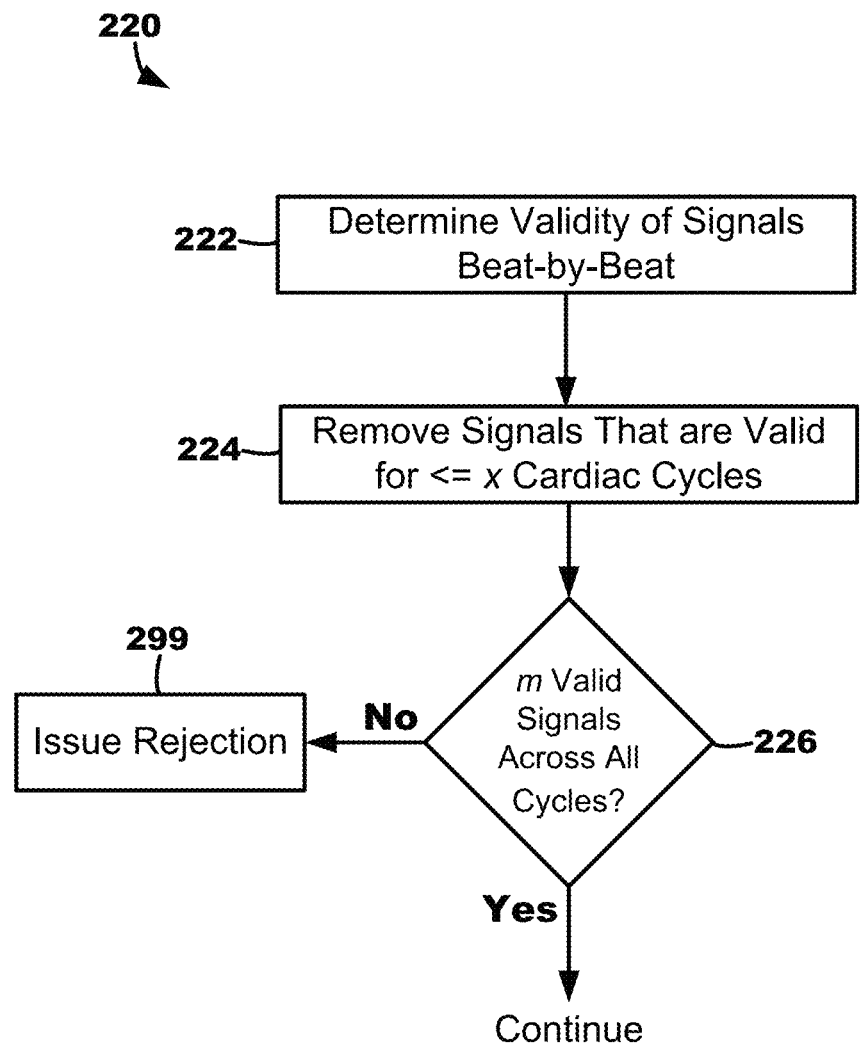
FIG. 6 is an illustrative method of removing invalid cardiac cycles.

One illustrative method of removing invalid cardiac signals 220 is depicted in FIG. 6. As shown, the validity of each electrode signal may be determined 222 similar to as described with respect to process 213 herein. Additionally, the process 222 may further evaluate whether the electrode signal is valid for a selected amount or number, x, of cardiac cycles, or beats, and if the electrode signal is valid for less that the selected amount or number, x, of cardiac cycles, then the electrode signal may be removed 224 and not further used to generate representative cardiac information. The selected amount or number, x, of cardiac cycles may be between 1 cardiac cycle and all cardiac cycles. In at least one embodiment, the selected amount or number, x, of cardiac cycles is all cardiac cycles.

The method, or process, 220 may then check to see if a selected number, m, valid electrode signals remain 226 after the removal processes 225. The selected number, m, of valid electrode signals may be between 5 valid electrode signals and 40 valid electrode signals. In at least one embodiment, the selected number, m, of valid electrode signals is 15 valid electrode signals. If the selected number, m, valid electrode signals remain after removal, then the method, or process, may continue 220. If the selected number, m, valid electrode signals do not remain after removal, then the method, or process, may issue a rejection 299. After the issuance of a rejection, a user or operator may be instructed to restart the method and recollect data using the plurality of electrodes in process 202. For example, if the selected number, m, of valid electrode signals is fifteen and less than fifteen valid electrode signals remain after removal of invalid valid electrode signals 224, then a data rejection may be issued 299.

The illustrative method 200 may further include removing uncorrelated cardiac cycles 230. The removal of uncorrelated cardiac cycles 230 may be based on various criteria of, or with respect to, the plurality of electrode signals over all the remaining cardiac cycles. In essence, it may be described that a template may be collected, or generated, for each cardiac cycle, and the templates may be compared to each other to determine how correlated, or uncorrelated, each cycle is to each other. Then, cardiac cycles that do not correlate well may be removed. Thus, representative cardiac information may then be generated based on electrical activity of only cardiac cycles that are relatively correlated.

Figure 7:
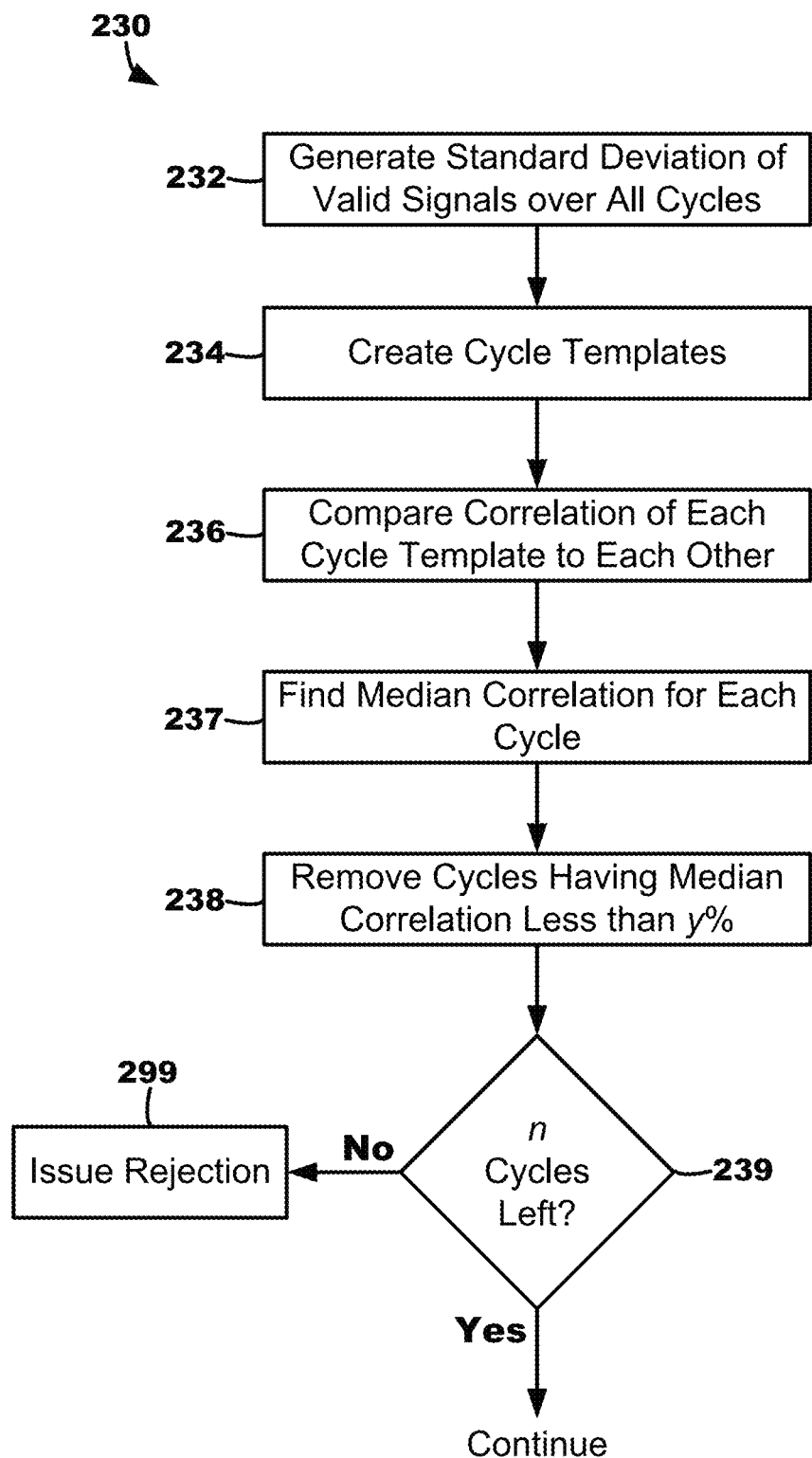
FIG. 7 is an illustrative method of removing uncorrelated cardiac cycles.

One illustrative method of removing uncorrelated cardiac cycles 230 is depicted in FIG. 7. As shown, a standard deviation, or another representative metric, may be generated across all valid remaining electrode signals over all remaining cardiac cycles 232. Another representative metric other than standard deviation that may be used with processes may be any other measure of statistical dispersion such as, e.g., mean deviation, interquartile deviation, range, etc.

Then, cardiac cycle templates may be generated for each cardiac cycle based on the standard deviation 234. For example, for each cardiac cycle, the timing of the peak (Tp) of the standard deviation signal may be determined, and then the signal may be windowed, or selected, from 75 milliseconds (ms) before and 75 ms after the Tp resulting in a single 150 ms long signal portion that is a templated for that cardiac cycle.

Then, each of the cardiac cycle templates may be compared to each other 236 to generate a correlation value associated with each comparison. Thus, a plurality of correlation values may be generated. In one embodiment, a correlation matrix may be generated. For example, if there are six detected cardiac cycles, comparison of each of the six detected cardiac cycles to each other will generate a six-by-six correlation matrix, with each cell including a correlation value. A median correlation, or another statistical metric, may be determined for each cardiac cycle from the plurality of correlation values 237 and any cardiac cycles having a median correlation less than correlation threshold, y %, may be removed 238. The correlation threshold, y %, may be between about 80% and 98%. In at least one embodiment, the correlation threshold, y %, may be 95%.

In other words, correlation of each cardiac cycle, or beat, template with respect to other cardiac cycles, or beats, may be generated, and then the median correlation of each cardiac cycle, or beat, may be identified. Then, for each beat, if the median correlation for the template of that beat with other detected beats is greater than or equal to 95%, then that beat is reasonably correlated. Conversely, for each beat, if the median correlation for the template of that beat with other detected beats is less than 95%, then that beat is may be removed.

Thus, uncorrelated cardiac cycles 230 may be removed to provide that uncorrelated cardiac cycles, or beats, may not be utilized to generate representative cardiac information. Thus, representative cardiac information may then be generated based only on electrical activity monitored that has correlated cardiac cycles.

The method, or process, 230 may then check to see if a selected number, n, cardiac cycles remain 239 after the removal process 238. The selected number, n, of cardiac cycles may be between 1 cardiac cycle and 5 cardiac cycles. In at least one embodiment, the selected number, n, is 2 cardiac cycles. If n cardiac cycles remain after removal, then the method, or process, may continue 230. If the selected n cardiac cycles do not remain after removal, then the method, or process, may issue a rejection 299. After the issuance of a rejection, a user or operator may be instructed to restart the method and recollect data using the plurality of electrodes in process 202. For example, if n is two and less than two cardiac cycles remain in the representative set of cardiac cycles after removing at least one cardiac cycle, then a data rejection may be issued 299.

The illustrative method 200 may further include removing inconsistent cardiac cycles 240. The removal of inconsistent cardiac cycles 240 may be based on various criteria or metrics of, or with respect to, the plurality of remaining cardiac cycles. For example, cardiac cycles may be ranked according to various criteria, and the cardiac cycles having the highest rank may be kept while other cardiac cycles may be removed. Further, for example, one or more metrics, such as, e.g., QRS duration, may be generated for each cardiac cycle and used to determined which cardiac cycles are consistent. Thus, representative cardiac information may then be generated based on only electrical activity of cardiac cycles that are consistent.

Figure 8:
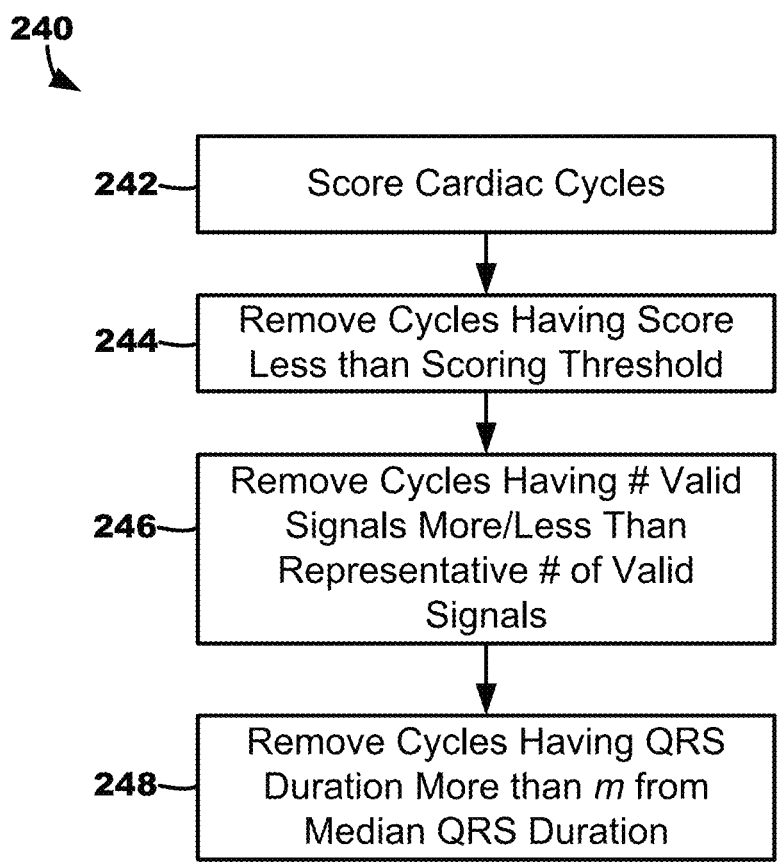
FIG. 8 is an illustrative method of removing inconsistent cardiac cycles.

One illustrative method of removing inconsistent cardiac cycles 240 is depicted in FIG. 8. As shown, the cardiac cycles may be scored and ranked 242 based one or more metrics generated thereon. For example, peak times, maximum amplitude, minimum amplitudes, amplitude sums of all valid electrode signals, various intervals such as R-wave to R-wave interval, etc. with respect to various fiducial points within electrical activity may be determined for each cardiac cycle. In one embodiment, the amplitude measures at the QRS peak may be utilized to score and rank the cardiac cycles. Such metrics may be used to rank the cardiac cycles, and then cardiac cycles below a selected rank threshold may be removed 244 from further consideration. In one or more embodiments, electrode signal validity determination may be described in U.S. Pat. App. Pub. No. 2019/0030331 A1 entitled "Cardiac Cycle Selection" published on Jan. 31, 2019, which is incorporated by reference herein in its entirety.

The method, or process, 240 may further include removing cardiac cycles having a number of valid electrode signals more/less than, or outside of a range of, a representative number or amount of valid electrode signals 246. The representative number or amount of valid electrode signals may be the median number of valid electrode signals for the remaining cardiac cycles. Thus, for each cardiac cycle, a difference (e.g., an absolute value) may be generated between the representative amount of valid electrode signals, which may be the median, and the number of valid electrode signals for that particular cycle. If the difference is less than a valid electrode signal range value, then the cardiac cycle may be determined to be consistent and may remain for further consideration. If the difference is greater than or equal to the valid electrode signal range value, then the cardiac cycle may be determined to be inconsistent and may be removed from further consideration.

For example, the valid electrode signal range value may be between about 2 and about 10. For example, if the valid electrode signal range value is 5 and the difference between representative number of valid electrode signals and the number of valid electrode signals for a particular cardiac cycle is 6, then the particular cardiac cycle may be removed from further consideration.

Additionally, in one or more embodiments, a cardiac cycle having more than representative number or amount of valid electrode signals and outside of the valid electrode signal range value may remain in the representative set of cardiac cycles (i.e., not removed). In other words, in this embodiment, the representative number of valid electrode signals may set the "floor" at which a cardiac cycle should have to remain, and the valid electrode signal range value represents a tolerance from the representative number of valid electrode signals.

The method, or process, 240 may further include removing cardiac cycles having a difference of a QRS duration from a representative QRS duration that is greater than a QRS range value 248. The QRS duration may be determined as described herein with respect to process 211. A representative QRS duration may be determined based on the plurality of generated QRS durations for the plurality of cardiac cycles. For example, a representative QRS duration may be the median QRS duration of the plurality of QRS durations of the plurality of cardiac cycles. A difference may be calculated, or generated, by subtracting the QRS duration of the current, or present, cardiac cycle from the representative QRS duration. The difference may then be compared to the QRS range value to determine whether the cardiac cycle is consistent and may remain or is inconsistent and may be removed. The QRS range value may between about 5 ms and about 35 ms.

In at least one embodiment, the QRS range value may be about 15 ms. Thus, if the median QRS duration is 105 ms and the QRS duration for a particular cardiac cycle is 97 ms, then it may be determined that the difference, 8 ms, is within the QRS range value, and therefore, the cardiac cycle is consistent and may remain. In this example, if the difference of a different cardiac cycle was 18 ms, and thus, greater than, or outside of, the QRS range value, then the different cardiac cycle is determined to be inconsistent and may be removed.

The illustrative method 200 may further include checking the remaining cardiac cycles for consistency 250. This consistency check may be completed, or executed, in a variety of different ways. One illustrative process of checking for consistency may include generating electrical heterogeneity information (EHI) for each remaining cardiac cycle based on the plurality of remaining electrode signals and then evaluating the generated EHI to each other to see if the EHI is consistent across all, or a selected number, of the remaining cardiac cycles.

The EHI may be described as information, or data, representative of at least one of mechanical cardiac functionality and electrical cardiac functionality. The EHI and other cardiac therapy information may be described in U.S. Pat. No. 9,486,151 entitled "METRICS OF ELECTRICAL DYSSYNCHRONY AND ELECTRICAL ACTIVATION PATTERNS FROM SURFACE ECG ELECTRODES" and issued on Nov. 8, 2016, which is hereby incorporated by reference it its entirety.

Electrical heterogeneity information (e.g., data) may be defined as information indicative of at least one of mechanical synchrony or dyssynchrony of the heart and/or electrical synchrony or dyssynchrony of the heart. In other words, electrical heterogeneity information may represent a surrogate of actual mechanical and/or electrical functionality of a patient's heart. In at least one embodiment, relative changes in electrical heterogeneity information (e.g., from baseline heterogeneity information to therapy heterogeneity information, from a first set of heterogeneity information to a second set of therapy heterogeneity information, etc.) may be used to determine a surrogate value representative of the changes in hemodynamic response (e.g., acute changes in LV pressure gradients). The left ventricular pressure may be typically monitored invasively with a pressure sensor located in the left ventricular of a patient's heart. As such, the use of electrical heterogeneity information to determine a surrogate value representative of the left ventricular pressure may avoid invasive monitoring using a left ventricular pressure sensor.

In at least one embodiment, the electrical heterogeneity information may include a standard deviation of ventricular activation times measured using some or all of the external electrodes, e.g., of the electrode apparatus 110. Further, local, or regional, electrical heterogeneity information may include standard deviations and/or averages of activation times measured using electrodes located in certain anatomic areas of the torso. For example, external electrodes on the left side of the torso of a patient may be used to compute local, or regional, left electrical heterogeneity information.

The electrical heterogeneity information may be generated using one or more various systems and/or methods. For example, electrical heterogeneity information may be generated using an array, or a plurality, of surface electrodes and/or imaging systems as described in U.S. Pat. No. 9,510,763 entitled "ASSESSING INTRA-CARDIAC ACTIVATION PATTERNS AND ELECTRICAL DYSSYNCHRONY" and issued on Dec. 6, 2016, U.S. Pat. No. 8,972,228 entitled "ASSESSING INTRA-CARDIAC ACTIVATION PATTERNS" and issued on Mar. 3, 2015, and U.S. Pat. No. 8,180,428 B2 entitled "METHODS AND SYSTEMS FOR USE IN SELECTING CARDIAC PACING SITES" and issued May 15, 2012, each of which is incorporated herein by reference in its entirety.

Electrical heterogeneity information may include one or more metrics or indices. For example, one of the metrics, or indices, of electrical heterogeneity may be a standard deviation of activation times (SDAT) measured using some or all of the electrodes on the surface of the torso of a patient. In some examples, the SDAT may be calculated using the estimated cardiac activation times over the surface of a model heart.

Another metric, or index, of electrical heterogeneity may be a left standard deviation of surrogate electrical activation times (LVED) monitored by external electrodes located proximate the left side of a patient. Further, another metric, or index, of electrical heterogeneity may include an average of surrogate electrical activation times (LVAT) monitored by external electrodes located proximate the left side of a patient. The LVED and LVAT may be determined (e.g., calculated, computed, etc.) from electrical activity measured only by electrodes proximate the left side of the patient, which may be referred to as "left" electrodes. The left electrodes may be defined as any surface electrodes located proximate the left ventricle, which includes region to left of the patient's sternum and spine. In one embodiment, the left electrodes may include all anterior electrodes on the left of the sternum and all posterior electrodes to the left of the spine. In another embodiment, the left electrodes may include all anterior electrodes on the left of the sternum and all posterior electrodes on the left side of the spine. In yet another embodiment, the left electrodes may be designated based on the contour of the left and right sides of the heart as determined using imaging apparatus (e.g., x-ray, fluoroscopy, etc.).

Another illustrative metric, or index, of dyssynchrony may be a range of activation times (RAT) that may be computed as the difference between the maximum and the minimum torso-surface or cardiac activation times, e.g., overall, or a region. The RAT reflects the span of activation times while the SDAT gives an estimate of the dispersion of the activation times from a mean. The SDAT also provides an estimate of the heterogeneity of the activation times, because if activation times are spatially heterogeneous, the individual activation times will be further away from the mean activation time, indicating that one or more regions of heart have been delayed in activation. In some examples, the RAT may be calculated using the estimated cardiac activation times over the surface of a model heart.

Another illustrative metric, or index, of electrical heterogeneity information may include estimates of a percentage of surface electrodes located within a particular region of interest for the torso or heart whose associated activation times are greater than a certain percentile, such as, for example the 70th percentile, of measured QRS complex duration or the determined activation times for surface electrodes. The region of interest may, e.g., be a posterior, left anterior, and/or left-ventricular region. The illustrative metric, or index, may be referred to as a percentage of late activation (PLAT). The PLAT may be described as providing an estimate of percentage of the region of interest, e.g., posterior and left-anterior area associated with the left ventricular area of heart, which activates late. A large value for PLAT may imply delayed activation of a substantial portion of the region, e.g., the left ventricle, and the potential benefit of electrical resynchronization through CRT by pre-exciting the late region, e.g., of left ventricle. In other examples, the PLAT may be determined for other subsets of electrodes in other regions, such as a right anterior region to evaluate delayed activation in the right ventricle. Furthermore, in some examples, the PLAT may be calculated using the estimated cardiac activation times over the surface of a model heart for either the whole heart or for a particular region, e.g., left or right ventricle, of the heart.

In one or more embodiments, the electrical heterogeneity information may include indicators of favorable changes in global cardiac electrical activation such as, e.g., described in Sweeney et al., "Analysis of Ventricular Activation Using Surface Electrocardiography to Predict Left Ventricular Reverse Volumetric Remodeling During Cardiac Resynchronization Therapy," Circulation, 2010 Feb. 9, 121(5): 626-34 and/or Van Deursen, et al., "Vectorcardiography as a Tool for Easy Optimization of Cardiac Resynchronization Therapy in Canine LBBB Hearts," Circulation Arrhythmia and Electrophysiology, 2012 Jun. 1, 5(3): 544-52, each of which is incorporated herein by reference in its entirety. Heterogeneity information may also include measurements of improved cardiac mechanical function measured by imaging or other systems to track motion of implanted leads within the heart as, e.g., described in Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, 2010 February, 21(2): 219-22, Sperzel et al., "Intraoperative Characterization of Interventricular Mechanical Dyssynchrony Using Electroanatomic Mapping System—A Feasibility Study," Journal of Interventional Cardiac Electrophysiology, 2012 November, 35(2): 189-96, and/or U.S. Pat. App. Pub. No. 2009/0099619 A1 entitled "METHOD FOR OPTIMIZING CRT THERAPY" and published on Apr. 16, 2009, each of which is incorporated herein by reference in its entirety.

Figure 9:
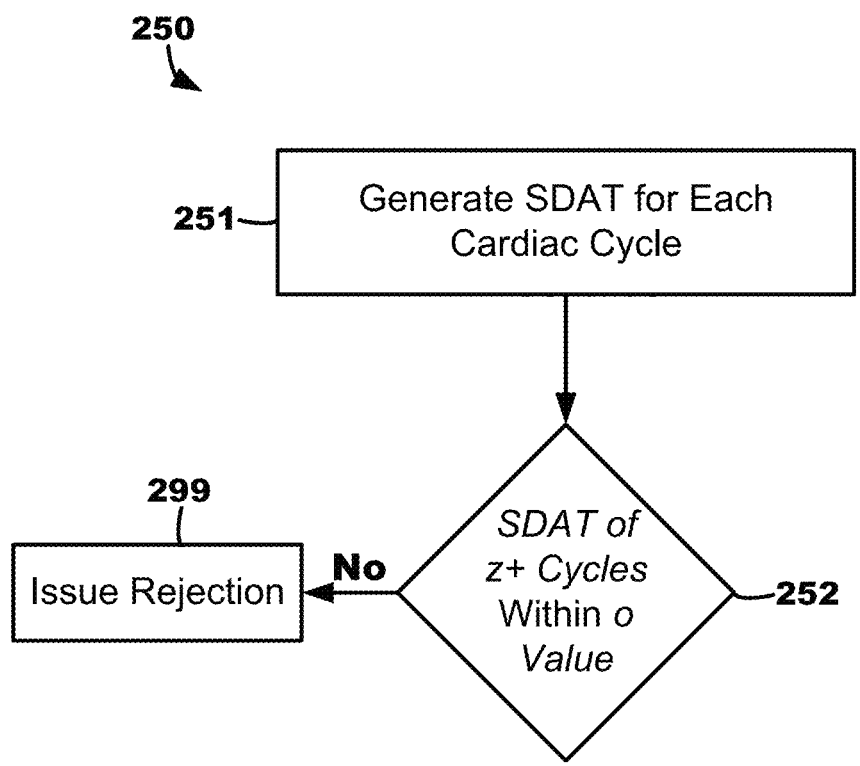
FIG. 9 is an illustrative method of checking remaining cardiac cycles for consistency.

One illustrative method 250 of checking remaining cardiac cycles for consistency is depicted in FIG. 9. In this example, SDAT is generated for each of the plurality of remaining cardiac cycles 251. Then, the method 250 may check if a selected number of cardiac cycles, z, result in EHI that is within a consistency value, o, 252. The selected number of cardiac cycles, z, may be between about 2 and 5 cardiac cycles. The consistency value, o, may be between about 2 ms and about 50 ms. In at least one embodiment, the selected number of cardiac cycles, z, is 2 and the consistency value, o, is 3.5 ms. Thus, in this example, a data rejection may be issued 299 if the SDAT of no two cardiac cycles of the plurality of remaining, or representative set, of cardiac cycles differ by less than or equal to 3.5 ms.

The illustrative method 200 may further include generating one or more metrics based on the remaining cardiac cycles 260. The remaining cardiac cycles may be referred to as the representative set of cardiac cycles since, e.g., the processes 210, 230, 240 have removed cardiac cycles that were determined, for one reason or another, to not be representative of the cardiac functionality of the patient. Various different metrics may be generated based on the electrical activity of the representative set of cardiac cycles. For example, one or more types of EHI may be generated based on the electrical activity of the representative set of cardiac cycles. In at least one embodiment, SDAT may be generated based on the electrical activity of the representative set of cardiac cycles.

Figure 10:
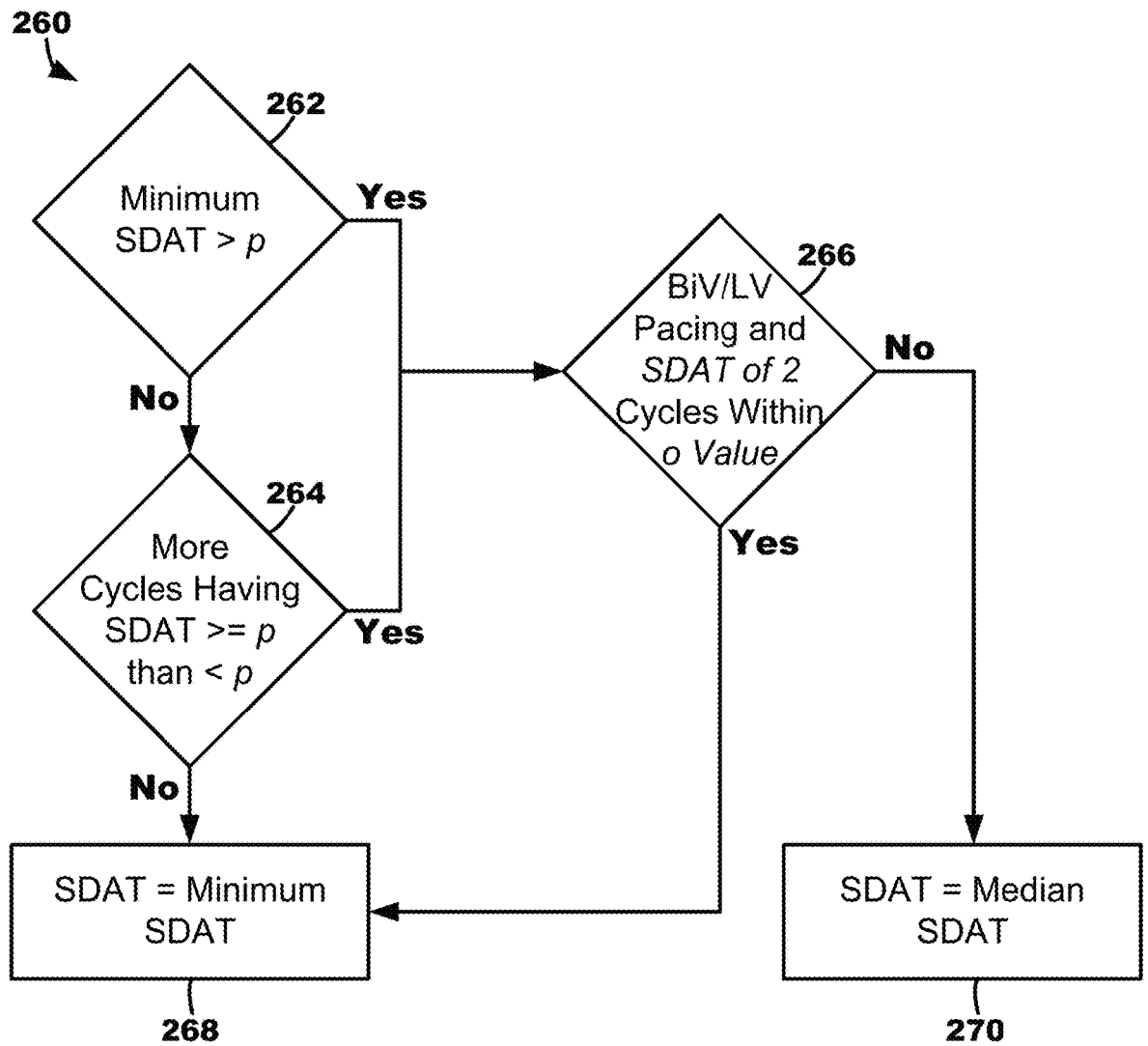
FIG. 10 is an illustrative method of generating a representative electrical heterogeneity information (EHI) based on the remaining cardiac cycles.

An illustrative method 260 of generating a representative electrical heterogeneity information (EHI), namely SDAT, based on the remaining, or representative set, cardiac cycles is depicted in FIG. 10. Generally, as shown, the SDAT may be set to either the minimum SDAT from the SDATs generated from the representative set of cardiac cycles 268 or the median SDAT from the SDATs generated from the representative set of cardiac cycles 270. First, the method 260 may include determining whether the minimum SDAT is less than or equal to or greater than a SDAT threshold, p, 262. The SDAT threshold, p, may be between about 10 ms and about 45 ms. In at least one embodiment, the SDAT threshold, p, may be 25 ms. If the minimum SDAT is less than or equal to p, then the method 260 may proceed to process 264, and conversely, if the minimum SDAT is greater than p, then the method 260 may proceed to process 266.

The method 260 may further include determining whether more cardiac cycles of the representative set of cardiac cycles have a SDAT than is greater than or equal to the SDAT threshold, p, than cardiac cycles of the representative set of cardiac cycles that have less than the SDAT threshold, p, 264. If the majority cardiac cycles of the representative set of cardiac cycles have a SDAT than is greater than or equal top, then the method 260 may proceed to process 266. Conversely, if a majority cardiac cycles of the representative set of cardiac cycles have a SDAT than is less than p, then the representative SDAT may be set to the minimum SDAT 268.

The method 260 may further include determining whether any left ventricular pacing is being delivered to the patient (e.g., left ventricular-only pacing, biventricular pacing, etc.) and whether the SDAT of at least two cardiac cycles of the representative set of cardiac cycles are within the consistency value, o, (e.g., 3.5 ms) of the minimum SDAT 266. If left ventricular pacing is being delivered and the SDAT of at least two cardiac cycles is within the consistency value, o, of the minimum SDAT, then the representative SDAT may be set to the minimum SDAT 268. Conversely, if left ventricular pacing is not being delivered or the SDAT of at least two cardiac cycles is not within the consistency value, o, of the minimum SDAT, then the representative SDAT may be set to the median SDAT 270.

Figure 11:
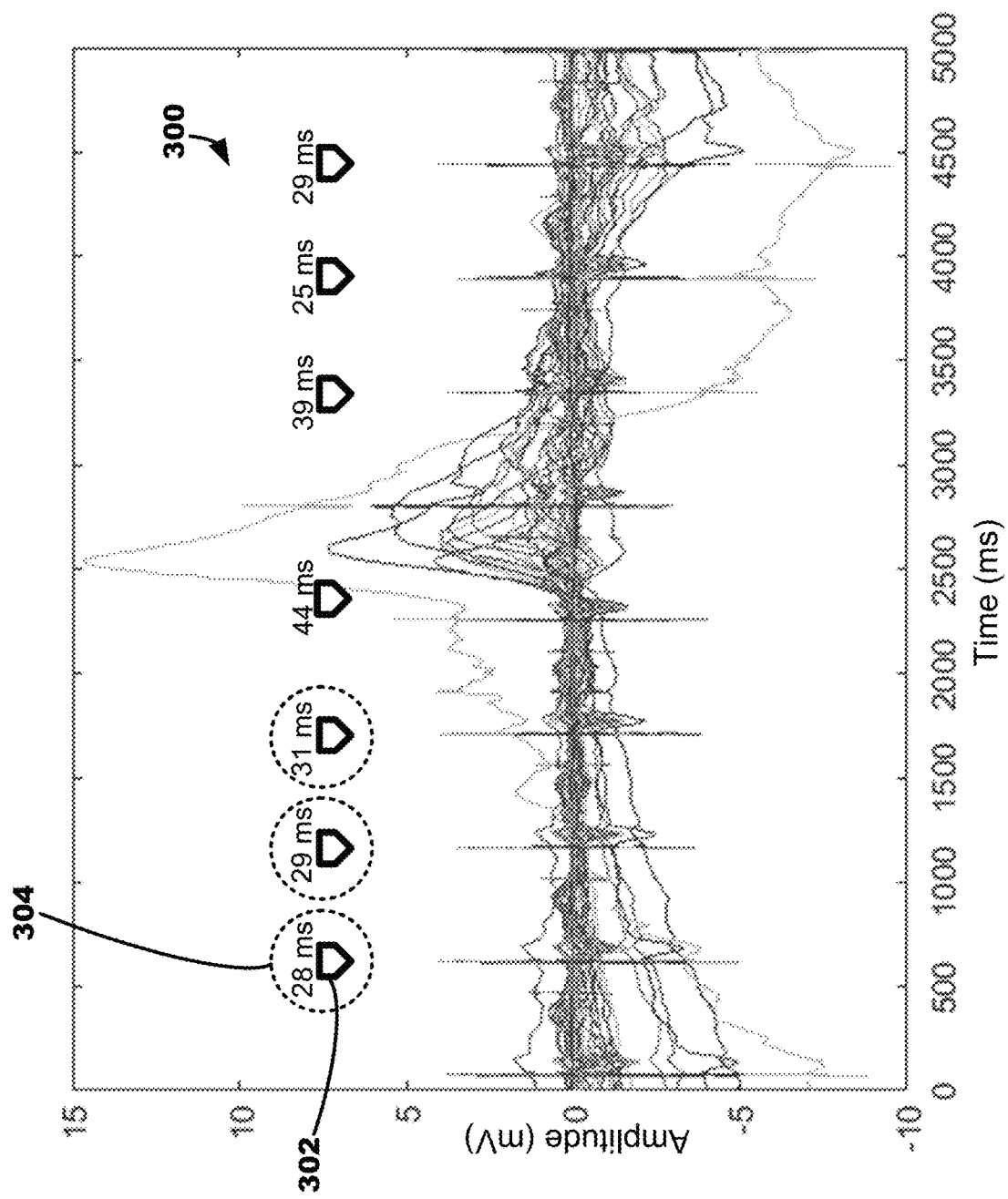
FIG. 11 depicts a plurality of electrode signals over a plurality of cardiac cycles.

A plurality of electrode signals over a plurality of cardiac cycles 300 are depicted in FIG. 11. Time in milliseconds is depicted on the x-axis and amplitude in millivolts of the electrode signals is depicted on the y-axis. As shown, seven cardiac cycles are detected within the plurality of electrode signals, each indicated by a chevron 302. Additionally, the SDAT of each of the cardiac cycles is depicted proximate the corresponding chevron.

The plurality of electrode signals over the plurality of cardiac cycles 300 were evaluated using the illustrative method 200 described herein. Four of the detected cardiac cycles were removed resulting in a representative set of cardiac cycles. Each of the representative set of cardiac cycles is indicted by a dashed-line circle 304 encircling the cardiac cycle's corresponding chevron. The representative set of cardiac cycles may then be used to determine the representative cardiac information such as, e.g., representative electrical heterogeneity information (EHI).

The plurality of electrode signals of each of the representative set of cardiac cycles of FIG. 11 are depicted in FIGS. 12A-12C. The first cardiac cycle of the representative set of cardiac cycles is depicted in FIG. 12A, the second cardiac cycle of the representative set of cardiac cycles is depicted in FIG. 12B, and the third cardiac cycle of the representative set of cardiac cycles is depicted in FIG. 12C, depict a plurality of electrode signals over three different cardiac cycles identified in FIG. 11.

The illustrative method 260 of generating representative EHI will now be utilized to generate, or select, the representative SDAT with the example depicted in FIG. 12. As shown, the minimum SDAT would be 28 ms and the median SDAT would be 29 ms. Assuming p=25 ms, then the minimum SDAT, 28 ms, is greater than p 262, and thus, the method 260 would proceed to process 266. Assuming left ventricular pacing is occurring and o is 3.5 ms, then the SDAT of two (in this case, all three) cardiac cycles are within the 3.5 ms of each other, and thus, the median SDAT, 29, is selected, or determined, to be the representative SDAT.

Figure 13:
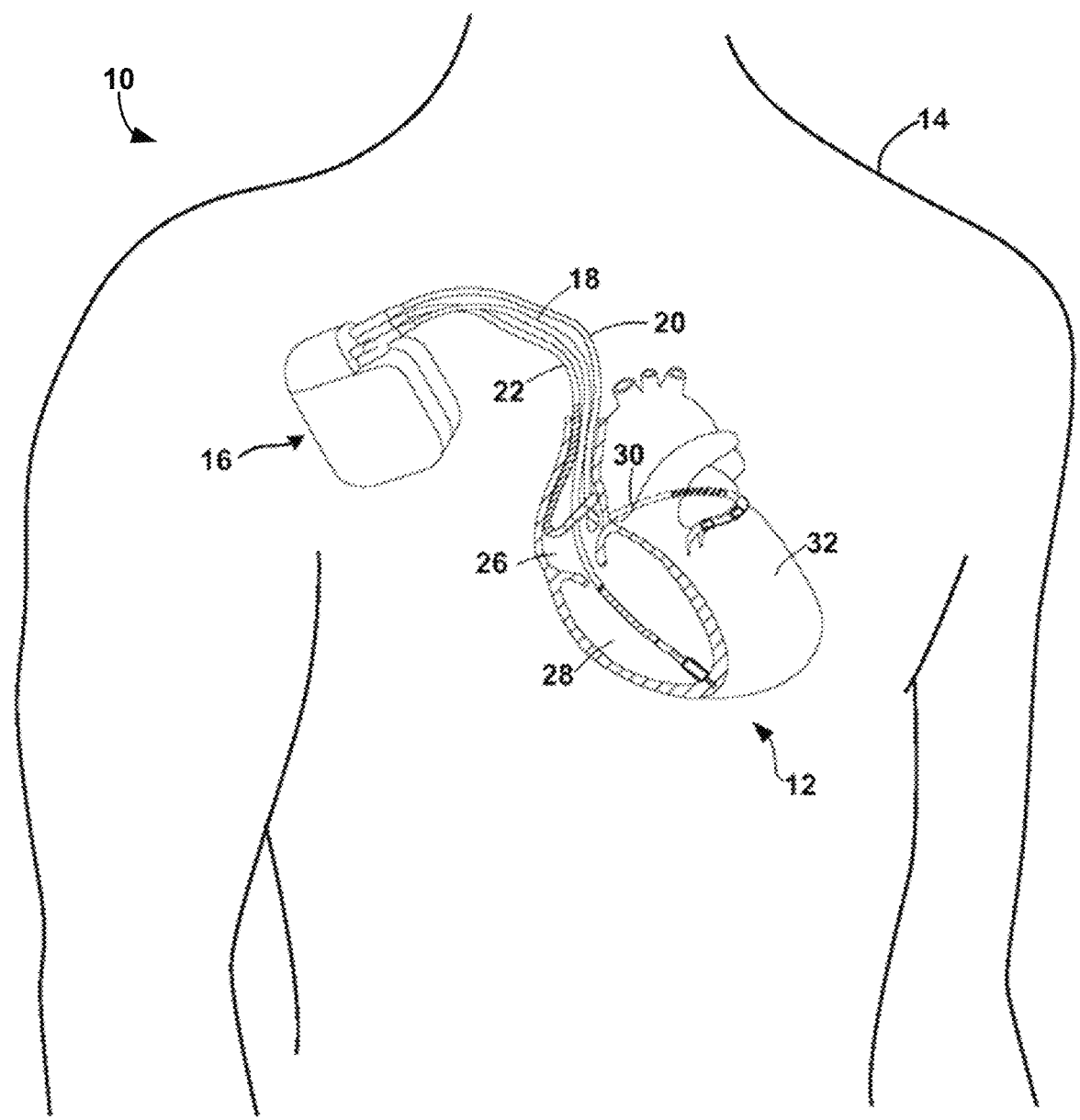
FIG. 13 is a diagram of an illustrative system including an illustrative implantable medical device (IMD).

Illustrative cardiac therapy systems and devices may be further described herein with reference to FIGS. 13-15 that may utilizes the illustrative systems, interfaces, methods, and processes described herein with respect to FIGS. 1-12.

FIG. 13 is a conceptual diagram illustrating an illustrative therapy system 10 that may be used to deliver pacing therapy to a patient 14. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 13, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., A-V delay and other various timings, pulse wide, amplitude, voltage, burst length, etc. Further, the IMD 16 may be operable to use various electrode configurations to deliver pacing therapy, which may be unipolar, bipolar, quadripoloar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 14A:
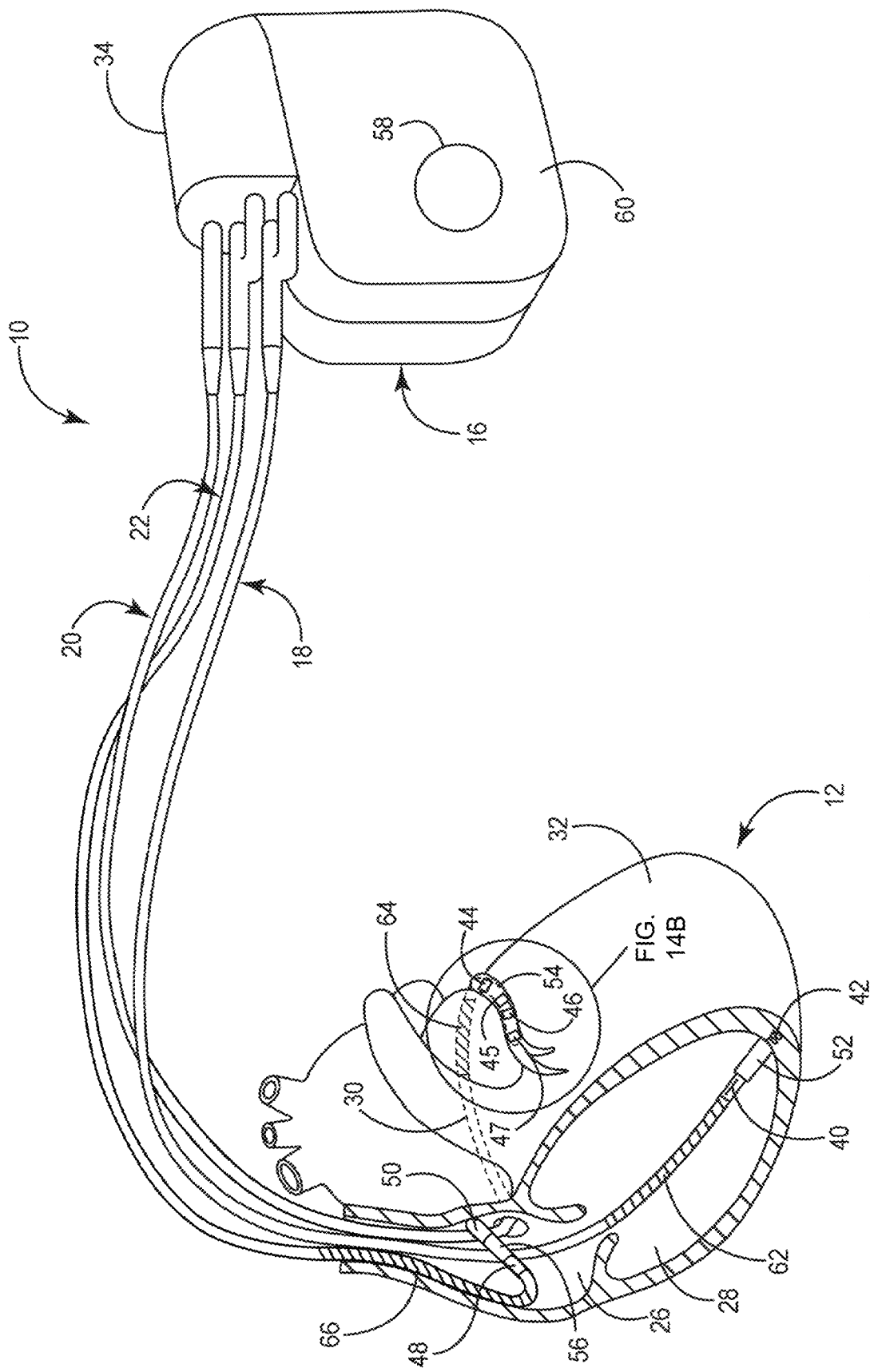
FIG. 14A is a diagram of the illustrative IMD of FIG. 13.
Figure 14B:
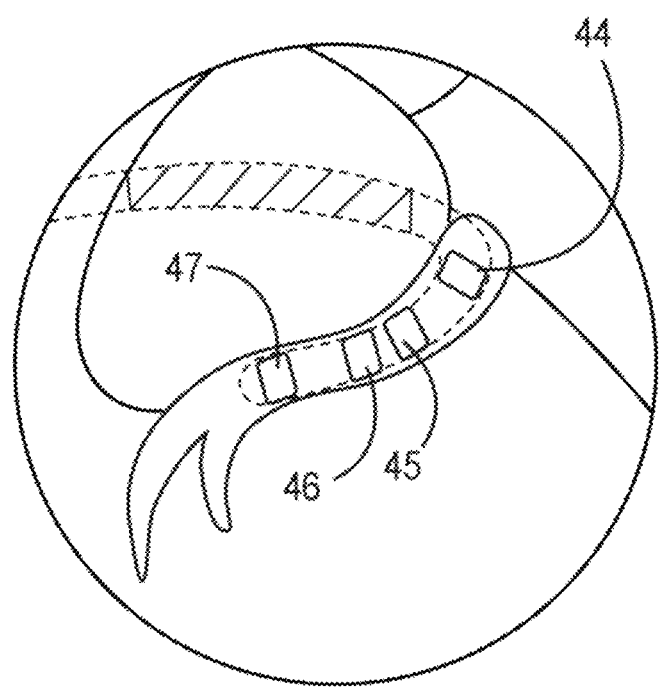
FIG. 14B is a diagram of an enlarged view of a distal end of the electrical lead disposed in the left ventricle of FIG. 14A.

FIGS. 14A-14B are conceptual diagrams illustrating the IMD 16 and the leads 18, 20, 22 of therapy system 10 of FIG. 13 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

Additionally, electrodes 44, 45, 46 and 47 may have an electrode surface area of about 5.3 mm$^2$ to about 5.8 mm$^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g. about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 14A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48, 50 may be used for unipolar sensing or pacing in combination with the housing electrode 58. It is generally understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 14A, the housing 60 may enclose a therapy delivery module that may include a stimulation generator for generating cardiac pacing pulses and defibrillation or cardioversion shocks, as well as a sensing module for monitoring the electrical signals of the patient's heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The configuration of the illustrative therapy system 10 illustrated in FIGS. 13-15 is merely one example. In other examples, the therapy system may include epicardial leads and/or patch electrodes instead of or in addition to the transvenous leads 18, 20, 22 illustrated in FIG. 13. Additionally, in other examples, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 13). Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 13-15. Still further, other therapy systems may include a single lead that extends from the IMD 16 into the right atrium 26 or the right ventricle 28, or two leads that extend into a respective one of the right atrium 26 and the right ventricle 28.

Figure 15A:
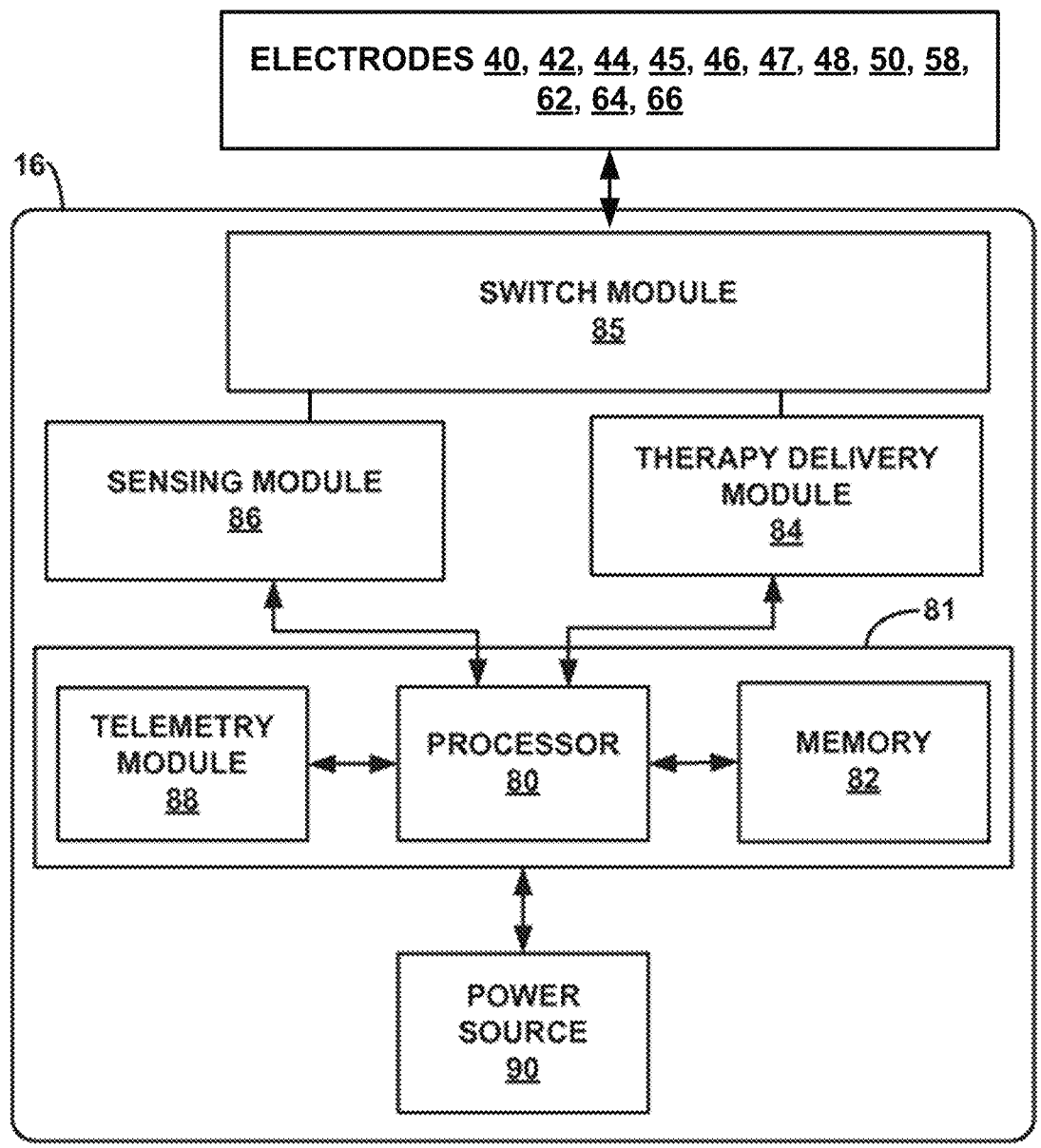
FIG. 15A is a block diagram of an illustrative IMD, e.g., of the systems of FIGS. 13-14.

FIG. 15A is a functional block diagram of one illustrative configuration of the IMD 16. As shown, the IMD 16 may include a control module 81, a therapy delivery module 84 (e.g., which may include a stimulation generator), a sensing module 86, and a power source 90.

The control module, or apparatus, 81 may include a processor 80, memory 82, and a telemetry module, or apparatus, 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically-erasable programmable ROM (EEPROM), flash memory, and/or any other digital media. An illustrative capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., A-V delays, V-V delays, pacing pulses with the amplitudes, pulse widths, frequency, or electrode polarities, etc., which may be specified by one or more selected therapy programs (e.g., A-V and/or V-V delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a bipolar or multipolar pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt-driven device and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 15B:
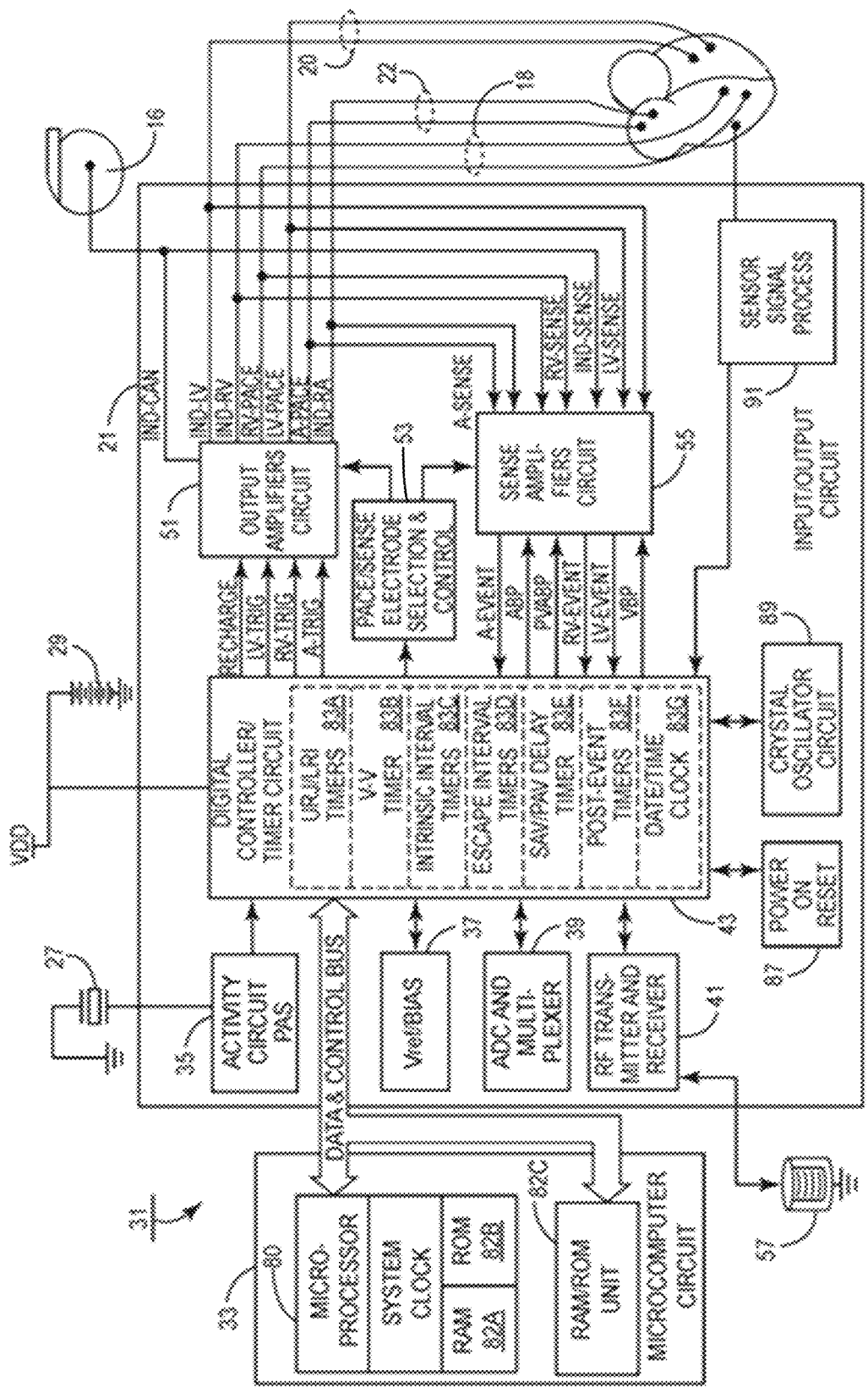
FIG. 15B is another block diagram of an illustrative IMD (e.g., an implantable pulse generator) circuitry and associated leads employed in the systems of FIGS. 13-14).

FIG. 15B is another embodiment of a functional block diagram for IMD 16 that depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 43 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers 55 for uplink transmission via RF transmitter and receiver circuit 41. Voltage reference and bias circuit 37, ADC and multiplexer 39, power-on-reset circuit 87, and crystal oscillator circuit 89 may correspond to any of those used in illustrative implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the patient activity sensor (PAS) circuit 35 in the depicted, illustrative IPG circuit 31. The patient activity sensor 27 is coupled to the IPG housing and may take the form of a piezoelectric crystal transducer. The output signal of the patient activity sensor 27 may be processed and used as an RCP. Sensor 27 generates electrical signals in response to sensed physical activity that are processed by activity circuit 35 and provided to digital controller/timer circuit 43. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which is incorporated herein by reference in its entirety. Similarly, the illustrative systems, apparatus, and methods described herein may be practiced in conjunction with alternate types of sensors such as oxygenation sensors, pressure sensors, pH sensors, and respiration sensors, for use in providing rate responsive pacing capabilities. Alternately, QT time may be used as a rate indicating parameter, in which case no extra sensor is required. Similarly, the illustrative embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities may include the ability to transmit stored digital information, e.g., operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative A-V delay intervals, V-V delay intervals, and the energy delivered to each ventricle and/or atrium.

In one embodiment, microprocessor 80 is a custom microprocessor adapted to fetch and execute instructions stored in RAM/ROM unit 82 in a conventional manner. It is contemplated, however, that other implementations may be suitable to practice the present disclosure. For example, an off-the-shelf, commercially available microprocessor or microcontroller, or custom application-specific, hardwired logic, or state-machine type circuit may perform the functions of microprocessor 80.

Digital controller/timer circuit 43 operates under the general control of the microcomputer 33 to control timing and other functions within the pacing circuit 21 and includes a set of timing and associated logic circuits of which certain ones pertinent to the present disclosure are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an A-V delay interval timer 83E for timing the A-LVp delay (or A-RVp delay) from a preceding A-EVENT or A-TRIG, a post-ventricular timer 83F for timing post-ventricular time periods, and a date/time clock 83G.

The A-V delay interval timer 83E is loaded with an appropriate delay interval for one ventricular chamber (e.g., either an A-RVp delay or an A-LVp) to time-out starting from a preceding A-PACE or A-EVENT. The interval timer 83E triggers pacing stimulus delivery and can be based on one or more prior cardiac cycles (or from a data set empirically derived for a given patient).

The post-event timer 83F times out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any A-V delay, and an atrial blanking period (ABP) during which atrial sensing is disabled. It should be noted that the starting of the post-atrial time periods and the A-V delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates A-V delays, V-V delays, post-ventricular time periods, and post-atrial time periods that vary with the sensor-based escape interval established in response to the RCP(s) and/or with the intrinsic atrial and/or ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. In order to trigger generation of an RV-PACE or LV-PACE pulse, digital controller/timer circuit 43 generates the RV-TRIG signal at the time-out of the A-RVp delay (in the case of RV pre-excitation) or the LV-TRIG at the time-out of the A-LVp delay (in the case of LV pre-excitation) provided by A-V delay interval timer 83E (or the V-V delay timer 83B). Similarly, digital controller/timer circuit 43 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND-CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory and can inadvertently be triggered by electrical noise signals or aberrantly conducted depolarization waves rather than true R-waves or P-waves.

The techniques described in this disclosure, including those attributed to the IMD 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by processing circuitry and/or one or more processors to support one or more aspects of the functionality described in this disclosure.

ILLUSTRATIVE EMBODIMENTS

Embodiment 1: A system for use in cardiac evaluation comprising:
  electrode apparatus comprising a plurality of external electrodes to monitor electrical activity from tissue of a patient; and
  a. a computing apparatus comprising processing circuitry and operably coupled to the electrode apparatus, the computing apparatus configured to:
    i. monitor electrical activity using the plurality of external electrodes resulting in a plurality of electrode signals over a plurality of cardiac cycles,
    ii. remove at least one unsatisfactory cardiac cycle from the plurality of cardiac cycles resulting in a representative set of cardiac cycles, and
    iii. generate representative electrical heterogeneity information (EHI) based on the monitored electrical activity of the representative set of cardiac cycles.

Embodiment 2: A method for use in cardiac evaluation comprising:
  a. monitoring electrical activity using a plurality of external electrodes from tissue of a patient resulting in a plurality of electrode signals over a plurality of cardiac cycles;
  removing at least one unsatisfactory cardiac cycle from the plurality of cardiac cycles resulting in a representative set of cardiac cycles; and
  generating representative electrical heterogeneity information (EHI) based on the monitored electrical activity of the representative set of cardiac cycles.

Embodiment 3: The system or method as set forth in any one of embodiments 1 and 2, wherein removing at least one unsatisfactory cardiac cycle from the plurality of cardiac cycles resulting in a representative set of cardiac cycles comprises:
  determining a QRS duration for each cardiac cycle based on the monitored electrical activity; and
  removing at least one cardiac cycle having a QRS duration less than or equal to a QRS duration threshold value.

Embodiment 4: The system or method as set forth in any one of embodiments 1-3, wherein removing at least one unsatisfactory cardiac cycle from the plurality of cardiac cycles resulting in a representative set of cardiac cycles comprises:
  a. determining the validity of each electrode signal of the plurality of electrode signals for each cardiac cycle; and
  b. removing at least one cardiac cycle having a number of valid electrode signals less than a valid electrode signal threshold.

Embodiment 5: The system or method as set forth in any one of embodiments 1-4, wherein the computing apparatus is further configured to issue a data rejection if less than two cardiac cycles remain in the representative set of cardiac cycles after removing at least one cardiac cycle.

Embodiment 6: The system or method as set forth in any one of embodiments 1-5, wherein the computing apparatus is further configured to:
  a. determining the validity of each electrode signal of the plurality of electrode signals across all of the plurality of cardiac cycles; and
  b. removing invalid electrode signals from the plurality of electrode signals over the plurality of cardiac cycles.

Embodiment 7: The system or method as set forth in embodiment 6, wherein the computing apparatus is further configured to issue a data rejection if less than a valid electrode signal threshold of the plurality of electrode signals are valid for all of the plurality of cardiac cycles.

Embodiment 8: The system or method as set forth in any one of embodiments 1-7, wherein removing at least one unsatisfactory cardiac cycle from the plurality of cardiac cycles resulting in a representative set of cardiac cycles comprises:
  a. comparing each of the plurality of cardiac cycles to each other resulting in a plurality of correlations values for each cardiac cycle;
  b. identifying a representative correlation value from the plurality of correlations values for each cardiac cycle; and
  c. removing at least one cardiac cycle having the representative correlation value less than a correlation threshold.

Embodiment 9: The system or method in embodiment 8, wherein removing at least one unsatisfactory cardiac cycle from the plurality of cardiac cycles resulting in a representative set of cardiac cycles further comprises:

a. generating a standard deviation of the plurality of electrode signals over the plurality of cardiac cycles; and
b. generating a cycle template for each of the plurality of cardiac cycles based on the standard deviation,
c. wherein comparing each of the plurality of cardiac cycles to each other resulting in a plurality of correlations values for each cardiac cycle comprises comparing each of the cycle templates of the plurality of cardiac cycles to each other resulting in the plurality of correlations values for each cardiac cycle.

Embodiment 10: The system or method as set forth in embodiment 9, wherein each cycle template comprises a portion of the standard deviation centered about a maximum value during the cardiac cycle.

Embodiment 11: The system or method as set forth in any one of embodiments 1-10, wherein removing at least one unsatisfactory cardiac cycle from the plurality of cardiac cycles resulting in a representative set of cardiac cycles comprises:
a. determining a score for each cardiac cycle of the plurality of cardiac cycles based on one or more morphological features of the plurality of electrode signals; and
removing at least one cardiac cycle having a score less than or equal to a scoring threshold value.

Embodiment 12: The system or method as set forth in any one of embodiments 1-11, wherein removing at least one unsatisfactory cardiac cycle from the plurality of cardiac cycles resulting in a representative set of cardiac cycles comprises:
determining the validity of each electrode signal of the plurality of electrode signals for each cardiac cycle of the plurality of cardiac cycles;
a. determining a number of valid electrode signals for each cardiac cycle of the plurality of cardiac cycles;
b. identifying a representative number of valid electrode signals based on the number of valid electrode signals for the plurality of cardiac cycles; and
removing at least one cardiac cycle having a difference of the number of valid electrode signals from the representative number of valid electrode signals that is less than a valid electrode signal range value.

Embodiment 13: The system or method as set forth in any one of embodiments 1-12, wherein removing at least one unsatisfactory cardiac cycle from the plurality of cardiac cycles resulting in a representative set of cardiac cycles comprises:
determining a QRS duration for each cardiac cycle based on the monitored electrical activity;
a. identifying a representative QRS duration based on the QRS durations of the plurality of cardiac cycles; and
removing at least one cardiac cycle having a difference of the QRS duration from the representative QRS duration that is less than a QRS range value.

Embodiment 14: The system or method as set forth in any one of embodiments 1-13, wherein the computing apparatus is further configured to:
a. generating electrical heterogeneity information (EHI) based on the monitored plurality of electrode signals for each cardiac cycle of the representative set of cardiac cycles; and
b. issuing a data rejection if the EHI of no two cardiac cycles of the representative set of cardiac cycles differ by less than a consistency value.

Embodiment 15: The system or method as set forth in embodiment 14, wherein the EHI comprises a standard deviation of electrical activation times monitored by the plurality of external electrodes, and wherein the consistency value comprises 3.5 milliseconds.

Embodiment 16: The system or method as set forth in any one of embodiments 1-15, wherein generating representative EHI based on the monitored electrical activity of the representative set of cardiac cycles comprises:
determining a standard deviation of electrical activation times (SDAT) based on the monitored plurality of electrode signals for each cardiac cycle of the representative set of cardiac cycles;
identifying a minimum SDAT of the representative set of cardiac cycles; and
setting the representative EHI as the minimum SDAT if the minimum SDAT is less than a SDAT threshold or if the SDAT of a majority of cardiac cycles of the representative set is less than the SDAT threshold.

Embodiment 17: The system or method as set forth in embodiment 16, wherein generating representative EHI based on the monitored electrical activity of the representative set of cardiac cycles further comprises:
a. setting the representative EHI as the minimum SDAT if left ventricular pacing is being delivered and the SDAT of at least two cardiac cycles are within a consistency value of the minimum SDAT; and
b. setting the representative EHI as the median SDAT of the representative set of cardiac cycles if left ventricular pacing is not being delivered or the SDAT of at least two cardiac cycles is not within the consistency value of the minimum SDAT.

Embodiment 18: A system for use in cardiac evaluation comprising:
a. electrode apparatus comprising a plurality of external electrodes to monitor electrical activity from tissue of a patient; and
b. a computing apparatus comprising processing circuitry and operably coupled to the electrode apparatus, the computing apparatus configured to:
i. monitor electrical activity using the plurality of external electrodes resulting in a plurality of electrode signals over a plurality of cardiac cycles,
ii. remove invalid signals from the plurality of electrode signals over the plurality of cardiac cycles resulting in a plurality of valid electrode signals over the plurality of cardiac cycles,
iii. remove unqualified cardiac cycles from the plurality of cardiac cycles based on the plurality of valid electrode signals over the plurality of cardiac cycles resulting in a qualified set of cardiac cycles,
iv. remove uncorrelated cardiac cycles from the qualified set of cardiac cycles based on the plurality of valid electrode signals over the qualified set of cardiac cycles resulting in a correlated set of cardiac cycles, and
v. remove inconsistent cardiac cycles from the correlated set of cardiac cycles based on the plurality of valid electrode signals over the correlated set of cardiac cycles resulting in a representative set of cardiac cycles.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A system for use in cardiac evaluation comprising:
electrode apparatus comprising a plurality of external electrodes to monitor electrical activity from tissue of a patient; and
a computing apparatus comprising processing circuitry and operably coupled to the electrode apparatus, the computing apparatus configured to:
monitor electrical activity using the plurality of external electrodes resulting in a plurality of electrode signals over a plurality of cardiac cycles,
remove at least one unsatisfactory cardiac cycle from the plurality of cardiac cycles resulting in a representative set of cardiac cycles, and
generate representative electrical heterogeneity information (EHI) based on the monitored electrical activity of the representative set of cardiac cycles.

2. The system of claim 1, wherein removing at least one unsatisfactory cardiac cycle from the plurality of cardiac cycles resulting in a representative set of cardiac cycles comprises:
determining a QRS duration for each cardiac cycle based on the monitored electrical activity; and
removing at least one cardiac cycle having a QRS duration less than or equal to a QRS duration threshold value.

3. The system of claim 1, wherein removing at least one unsatisfactory cardiac cycle from the plurality of cardiac cycles resulting in a representative set of cardiac cycles comprises:
determining the validity of each electrode signal of the plurality of electrode signals for each cardiac cycle; and
removing at least one cardiac cycle having a number of valid electrode signals less than a valid electrode signal threshold.

4. The system of claim 1, wherein the computing apparatus is further configured to issue a data rejection if less than two cardiac cycles remain in the representative set of cardiac cycles after removing at least one cardiac cycle.

5. The system of claim 1, wherein the computing apparatus is further configured to:
determining the validity of each electrode signal of the plurality of electrode signals across all of the plurality of cardiac cycles; and
removing invalid electrode signals from the plurality of electrode signals over the plurality of cardiac cycles.

6. The system of claim 5, wherein the computing apparatus is further configured to issue a data rejection if less than a valid electrode signal threshold of the plurality of electrode signals are valid for all of the plurality of cardiac cycles.

7. The system of claim 1, wherein removing at least one unsatisfactory cardiac cycle from the plurality of cardiac cycles resulting in a representative set of cardiac cycles comprises:
comparing each of the plurality of cardiac cycles to each other resulting in a plurality of correlations values for each cardiac cycle;
identifying a representative correlation value from the plurality of correlations values for each cardiac cycle; and
removing at least one cardiac cycle having the representative correlation value less than a correlation threshold.

8. The system of claim 7, wherein removing at least one unsatisfactory cardiac cycle from the plurality of cardiac cycles resulting in a representative set of cardiac cycles further comprises:
generating a standard deviation of the plurality of electrode signals over the plurality of cardiac cycles; and
generating a cycle template for each of the plurality of cardiac cycles based on the standard deviation,
wherein comparing each of the plurality of cardiac cycles to each other resulting in a plurality of correlations values for each cardiac cycle comprises comparing each of the cycle templates of the plurality of cardiac cycles to each other resulting in the plurality of correlations values for each cardiac cycle.

9. The system of claim 8, wherein each cycle template comprises a portion of the standard deviation centered about a maximum value during the cardiac cycle.

10. The system of claim 1, wherein removing at least one unsatisfactory cardiac cycle from the plurality of cardiac cycles resulting in a representative set of cardiac cycles comprises:
determining a score for each cardiac cycle of the plurality of cardiac cycles based on one or more morphological features of the plurality of electrode signals; and
removing at least one cardiac cycle having a score less than or equal to a scoring threshold value.

11. The system of claim 1, wherein removing at least one unsatisfactory cardiac cycle from the plurality of cardiac cycles resulting in a representative set of cardiac cycles comprises:
determining the validity of each electrode signal of the plurality of electrode signals for each cardiac cycle of the plurality of cardiac cycles;
determining a number of valid electrode signals for each cardiac cycle of the plurality of cardiac cycles;
identifying a representative number of valid electrode signals based on the number of valid electrode signals for the plurality of cardiac cycles; and
removing at least one cardiac cycle having a difference of the number of valid electrode signals from the representative number of valid electrode signals that is less than a valid electrode signal range value.

12. The system of claim 1, wherein removing at least one unsatisfactory cardiac cycle from the plurality of cardiac cycles resulting in a representative set of cardiac cycles comprises:
determining a QRS duration for each cardiac cycle based on the monitored electrical activity;
identifying a representative QRS duration based on the QRS durations of the plurality of cardiac cycles; and
removing at least one cardiac cycle having a difference of the QRS duration from the representative QRS duration that is less than a QRS range value.

13. The system of claim 1, wherein the computing apparatus is further configured to:
generating electrical heterogeneity information (EHI) based on the monitored plurality of electrode signals for each cardiac cycle of the representative set of cardiac cycles; and
issuing a data rejection if the EHI of no two cardiac cycles of the representative set of cardiac cycles differ by less than a consistency value.

14. The system of claim 13, wherein the EHI comprises a standard deviation of electrical activation times monitored by the plurality of external electrodes, and wherein the consistency value comprises 3.5 milliseconds.

15. The system of claim 1, wherein generating representative EHI based on the monitored electrical activity of the representative set of cardiac cycles comprises:
    determining a standard deviation of electrical activation times (SDAT) based on the monitored plurality of electrode signals for each cardiac cycle of the representative set of cardiac cycles;
    identifying a minimum SDAT of the representative set of cardiac cycles; and
    setting the representative EHI as the minimum SDAT if the minimum SDAT is less than a SDAT threshold or if the SDAT of a majority of cardiac cycles of the representative set is less than the SDAT threshold.

16. The system of claim 15, wherein generating representative EHI based on the monitored electrical activity of the representative set of cardiac cycles further comprises:
    setting the representative EHI as the minimum SDAT if left ventricular pacing is being delivered and the SDAT of at least two cardiac cycles are within a consistency value of the minimum SDAT; and
    setting the representative EHI as the median SDAT of the representative set of cardiac cycles if left ventricular pacing is not being delivered or the SDAT of at least two cardiac cycles is not within the consistency value of the minimum SDAT.

17. A method for use in cardiac evaluation comprising:
    monitoring electrical activity using a plurality of external electrodes from tissue of a patient resulting in a plurality of electrode signals over a plurality of cardiac cycles;
    removing at least one unsatisfactory cardiac cycle from the plurality of cardiac cycles resulting in a representative set of cardiac cycles;
    generating representative electrical heterogeneity information (EHI) based on the monitored electrical activity of the representative set of cardiac cycles; and
    configuring a cardiac therapy provided by an implantable medical device.

18. The method of claim 17, wherein removing at least one unsatisfactory cardiac cycle from the plurality of cardiac cycles resulting in a representative set of cardiac cycles comprises:
    determining a QRS duration for each cardiac cycle based on the monitored electrical activity; and
    removing at least one cardiac cycle having a QRS duration less than or equal to a QRS duration threshold value.

19. The method of claim 17, wherein removing at least one unsatisfactory cardiac cycle from the plurality of cardiac cycles resulting in a representative set of cardiac cycles comprises:
    determining the validity of each electrode signal of the plurality of electrode signals for each cardiac cycle; and
    removing at least one cardiac cycle having a number of valid electrode signals less than a valid electrode signal threshold.

20. The method of claim 17, wherein the method further comprises issuing a data rejection if less than two cardiac cycles remain in the representative set of cardiac cycles after removing at least one cardiac cycle.

21. The method of claim 17, wherein the method further comprises:
    determining the validity of each electrode signal of the plurality of electrode signals across all of the plurality of cardiac cycles; and
    removing invalid electrode signals from the plurality of electrode signals over the plurality of cardiac cycles.

22. The method of claim 21, wherein the method further comprises issuing a data rejection if less than a valid electrode signal threshold of the plurality of electrode signals is valid for all of the plurality of cardiac cycles.

23. The method of claim 17, wherein removing at least one unsatisfactory cardiac cycle from the plurality of cardiac cycles resulting in a representative set of cardiac cycles comprises:
    comparing each of the plurality of cardiac cycles to each other resulting in a plurality of correlations values for each cardiac cycle;
    identifying a representative correlation value from the plurality of correlations values for each cardiac cycle; and
    removing at least one cardiac cycle having the representative correlation value less than a correlation threshold.

24. The method of claim 23, wherein removing at least one unsatisfactory cardiac cycle from the plurality of cardiac cycles resulting in a representative set of cardiac cycles further comprises:
    generating a standard deviation of the plurality of electrode signals over the plurality of cardiac cycles; and
    generating a cycle template for each of the plurality of cardiac cycles based on the standard deviation,
    wherein comparing each of the plurality of cardiac cycles to each other resulting in a plurality of correlations values for each cardiac cycle comprises comparing each of the cycle templates of the plurality of cardiac cycles to each other resulting in the plurality of correlations values for each cardiac cycle.

25. The method of claim 24, wherein each cycle template comprises a portion of the standard deviation centered about a maximum value during the cardiac cycle.

26. The method of claim 17, wherein removing at least one unsatisfactory cardiac cycle from the plurality of cardiac cycles resulting in a representative set of cardiac cycles comprises:
    determining a score for each cardiac cycle of the plurality of cardiac cycles based on one or more morphological features of the plurality of electrode signals; and
    removing at least one cardiac cycle having a score less than or equal to a scoring threshold value.

27. The method of claim 17, wherein removing at least one unsatisfactory cardiac cycle from the plurality of cardiac cycles resulting in a representative set of cardiac cycles comprises:
    determining the validity of each electrode signal of the plurality of electrode signals for each cardiac cycle of the plurality of cardiac cycles;
    determining a number of valid electrode signals for each cardiac cycle of the plurality of cardiac cycles;
    identifying a representative number of valid electrode signals based on the number of valid electrode signals for the plurality of cardiac cycles; and
    removing at least one cardiac cycle having a difference of the number of valid electrode signals from the representative number of valid electrode signals that is less than a valid electrode signal range value.

28. The method of claim 17, wherein removing at least one unsatisfactory cardiac cycle from the plurality of cardiac cycles resulting in a representative set of cardiac cycles comprises:
    determining a QRS duration for each cardiac cycle based on the monitored electrical activity;
    identifying a representative QRS duration based on the QRS durations of the plurality of cardiac cycles; and removing at least one cardiac cycle having a difference of the QRS duration from the representative QRS duration that is less than a QRS range value.

29. The method of claim 17, wherein the method further comprises:
generating electrical heterogeneity information (EHI) based on the monitored plurality of electrode signals for each cardiac cycle of the representative set of cardiac cycles; and
issuing a data rejection if the EHI of no two cardiac cycles of the representative set of cardiac cycles differ by less than a consistency value.

30. The method of claim 29, wherein the EHI comprises a standard deviation of electrical activation times monitored by the plurality of external electrodes, and wherein the consistency value comprises 3.5 milliseconds.

31. The method of claim 17, wherein generating representative EHI based on the monitored electrical activity of the representative set of cardiac cycles comprises:
determining a standard deviation of electrical activation times (SDAT) based on the monitored plurality of electrode signals for each cardiac cycle of the representative set of cardiac cycles;
identifying a minimum SDAT of the representative set of cardiac cycles; and
setting the representative EHI as the minimum SDAT if the minimum SDAT is less than a SDAT threshold or if the SDAT of a majority of cardiac cycles of the representative set is less than the SDAT threshold.

32. The method of claim 31, wherein generating representative EHI based on the monitored electrical activity of the representative set of cardiac cycles further comprises:
setting the representative EHI as the minimum SDAT if left ventricular pacing is being delivered and the SDAT of at least two cardiac cycles are within a consistency value of the minimum SDAT; and
setting the representative EHI as the median SDAT of the representative set of cardiac cycles if left ventricular pacing is not being delivered or the SDAT of at least two cardiac cycles is not within the consistency value of the minimum SDAT.

33. A system for use in cardiac evaluation comprising:
electrode apparatus comprising a plurality of external electrodes to monitor electrical activity from tissue of a patient; and
a computing apparatus comprising processing circuitry and operably coupled to the electrode apparatus, the computing apparatus configured to:
monitor electrical activity using the plurality of external electrodes resulting in a plurality of electrode signals over a plurality of cardiac cycles,
remove invalid signals from the plurality of electrode signals over the plurality of cardiac cycles resulting in a plurality of valid electrode signals over the plurality of cardiac cycles,
remove unqualified cardiac cycles from the plurality of cardiac cycles based on the plurality of valid electrode signals over the plurality of cardiac cycles resulting in a qualified set of cardiac cycles,
remove uncorrelated cardiac cycles from the qualified set of cardiac cycles based on the plurality of valid electrode signals over the qualified set of cardiac cycles resulting in a correlated set of cardiac cycles, and
remove inconsistent cardiac cycles from the correlated set of cardiac cycles based on the plurality of valid electrode signals over the correlated set of cardiac cycles resulting in a representative set of cardiac cycles.

* * * * *